United States Patent [19]
Hamilton et al.

[11] Patent Number: 5,296,688
[45] Date of Patent: Mar. 22, 1994

[54] APPARATUS AND METHOD FOR RECORDING PROGRESS NOTES

[76] Inventors: David W. Hamilton, 5950 Bartholomew Dr., Lincoln, Nebr. 68512; David J. Kats, 1725 S. 33rd St., Lincoln, Nebr. 68506

[21] Appl. No.: 824,575

[22] Filed: Jan. 23, 1992

Related U.S. Application Data

[63] Continuation of Ser. No. 444,897, Dec. 4, 1989, abandoned.

[51] Int. Cl.$^5$ .............................................. G06F 15/42
[52] U.S. Cl. ................................. 235/375; 364/413.02
[58] Field of Search ............ 235/375; 364/419, 413.02

[56] References Cited
U.S. PATENT DOCUMENTS

| | | | |
|---|---|---|---|
| 4,459,049 | 7/1984 | Howell et al. | 364/419 |
| 4,502,128 | 2/1985 | Okajima et al. | 364/419 |
| 4,835,372 | 5/1989 | Gombrich et al. | 235/462 |
| 5,006,699 | 4/1991 | Felkner et al. | 235/375 |

Primary Examiner—Richard A. Rosenberger
Attorney, Agent, or Firm—John A. Beehner

[57] ABSTRACT

An apparatus and method for reporting progress notes includes a system wherein a collection of bar encoded input data is selectively scanned by a portable hand-held wand. Stored data is downloaded from the wand at the end of a day or session into a computer which edits the data into phrases, combines the phrases into sentences and the sentences into paragraphs to produce an organized readable full text report without any manual writing, dictation, or transcription.

17 Claims, 11 Drawing Sheets

| | | | | | | | | |
|---|---|---|---|---|---|---|---|---|
| SERVICES | OCCIPUT | C1 | C2 | C3 | C4 | C5 | C6 | C7 |
| T1 | T2 | T3 | T4 | T5 | T6 | T7 | T8 | T9 |
| T10 | T11 | T12 | ADJ. & ULTRASOUND | ADJ. & EMS | | | | |
| L1 | L2 | L3 | L4 | L5 | | | | |
| ELECMUSCLE STIMULATION | ULTRASOUND | HOT PACKS | COLD PACKS | CERVICAL TRACTION | LEFT ILIUM | RIGHT ILIUM | SACRUM | COCCYX |
| | | | | | LUMBAR TRACTION | MOTORIZED TRACTION | DIATHERMY | |
| TREATMENT TODAY | SPINAL ADJ. (GENERAL) | | | | | CANCEL | ACCEPT | ACCEPT |

| SMITH CHIROPRACTIC CENTER | | |
|---|---|---|
| PATIENT CODE | PATIENT ACCOUNT | PATIENT |
| P0000001 | 1867 | WENDI WIEDEMAN<br>3130 O ST<br>LINCOLN          NE   68510 |
| P0000002 | 222 22 2222 | SUPER WOMAN<br>919 EAST AVENUE<br>HOLDREGE       NE   68949 |
| P0000003 | 505 78 8377 | THE INCREDIBLE HULK<br>4311"E" STREET<br>LINCOLN          NE   68510 |
| P0000004 | 111 22 333 | MICKEY M. MOUSE<br><br>                 NE   68510 |
| P0000005 | 23456 | DONALD DUCK<br>555 S.W. PATIENT STREET<br>DUCK CITY       NE   68500 |
| P0000006 | 987654 | MAD MAX<br>656 NORTH WEST AVENUE<br>SOMECITY        NE   68555 |

```
REPORT OF SEE DOCTOR                         DOCTOR: CARSON
ENTRIES IN PATIENT
CAS NOTES.                                        12/19/88
                                                  PAGE#  1
------------------------------------------------------------

SUPER WOMAN   P0000003/3033033  ---  VISIT: 11/19/88@12:33 AM

PATIENT INTERED THE OFFICE COMPLAININ OF PELVIC ACHING CHILLS
WHILE SLEEPING EXAMINATION OF THE PATIENT REVEALED A LONG RIGHT LEG
DECREASED HEAT READING BY INSTRUMENT BRUSING POSITIVE OR ABNORMAL LEG
RAISER THE PATIENT IS (*SEE DOCTOR*) PATIENT SHOULD BE SEEN TWICE
DAILY

DOCTOR'S:
COMMENTS: _____
_____
_____
_____

GEORGE C. WASHINGTON  P0000006/60060660 - VISIT: 11/19/88@12:34 AM (*SEE DOCTOR*)

DOCTOR'S:
COMMENTS: _____
_____
_____
_____
```

FIG. 16

APPARATUS AND METHOD FOR RECORDING PROGRESS NOTES

CROSS REFERENCE TO RELATED APPLICATION

This is a continuation of patent application Ser. No. 07/444,897 filed Dec. 4, 1989, now abandoned.

BACKGROUND OF THE INVENTION

1. Technical Field

The present invention is directed generally to an apparatus and method for recording progress notes and more particularly to such a system wherein words and phrases entered by a bar code wand are edited into complete grammatically correct English sentences to enable the instantaneous preparation of full text progress notes in no more time that it takes a practitioner to scan the selected applicable bar codes of an appropriate wall chart.

An increasing amount of time for any doctor or other health care practitioner is spent in the preparation of notes to document office visits and treatments. Handwritten notes are often unacceptable to insurance companies when processing claims; may be illegible to a typist transcribing the notes; and may not be consistent and uniform between different practitioners in the same office. To assure complete consistent printed notes while eliminating transcribing time, an improved system for recording progress notes has been developed.

The development of the art at the time of the invention is at least partially evidenced by an article by Gilbert R. Jost in the March, 1986 edition of *Radiologic Clinics of North America*, Volume 24, No. 1, pages 19-26. That article describes various computerized systems for facilitating the dictation and transcription of medical report and includes a brief description of the use of bar codes at page 23. Absent an automatic editing capability, however, such a system has limited utility. If the bar encoded entry data is drafted into substantially complete sentences, the flexibility of the data entry system suffers. If the data entry possibilities are increased in numbers to cover substantially every conceivable possibility, a library of entry data becomes so cumbersome as to be substantially inoperative. Finally, if the output reports are not set out in an easily readable and understandable format, they may be unacceptable by insurance companies or for permanent patient records so as to require further editing and revision by the practitioner.

Accordingly, a primary object of the invention is to provide an improved apparatus and method for recording progress notes.

Another object is to provide such a system wherein bar coded input words and phrases are automatically edited into grammatically correct full sentences of a progress notes report.

Another object is to provide such a system which affords maximum flexibility of input information from a minimum number of data entry bar codes.

Another object is to provide such a system which accommodates customization of bar coded input data for adaptation to a particular practitioner or field of use.

Another object is to provide such a system which is readily installed in a practitioner's office without interference with existing computer systems.

Another object is to provide such a system which can be quickly and easily learned by a practitioner.

Another object is to provide such a system which eliminates the taking of tedious manual notes, together with the transcription thereof and the usual communications between the notes preparer and transcriber.

Finally, an object of the invention is to provide such a system which is cost efficient, easy to use and capable of automatically producing legible organized reports from a practitioner's original bar coded input data.

SUMMARY OF THE INVENTION

The apparatus and method for recording progress notes according to the invention involves taking notes with the use of a bar code reader. Bar code input data is arranged on any of a variety of wall charts, booklets, pocket cards and flip charts which may be laid out as a collection of bar codes, each identified by a one word mnemonic. The bar codes are arranged in subsets to be efficient for the user taking the notes. With a hand-held portable wand, the user scans multiple bar codes, each associated with a mnemonic. When notes for a given number of patients or subjects are completed, the raw scanned data is transferred into a computer database which keeps the notes in a relational database for orderly later recall. Each bit of data is tagged with the date and time of the scan, giving a record of when the notes were made.

When the user wishes to recall his or her notes, the computer translates each of the raw scans into a phrase. It then combines the phrases into sentences and sentences into paragraphs. To combine the disjointed phrases into readable sentences, the system uses a hashing technique to instantly classify these phrases as if they were simple elements of English, i.e., nouns, verbs, adverbs, etc. Thus, complete sentences can be built form disjointed phrases by one of three processes:

(1) The injection of punctuation;
(2) The addition of conjunctives or conjunctive phrases; and
(3) Phrase rearrangement.

This building of text, in order to be useful, required the invention of a rapid lookup structure to assign a numeric value to each scanned phrase. These numeric values represent how each phrase would be treated if it were an English element. A system requirement, therefore, was lookup speed which would be acceptable to the user. The technique invented was to develop a method to load into computer RAM memory an array which simulated a table in the softwares relational database. This RAM array gives a much quicker lookup of the numeric values than could be accomplished using traditional disc media storage based database lookup techniques.

The improvements presented by the present invention thus include a computer programmed to be capable of editing input information and structuring it in organized readable sentences; a wand capable of reading, storing and downloading all reports for a given day, or portion of a day; and the use of the portable wand in combination with a wall chart or other library of bar codes conveniently mounted adjacent an examining area for immediate report preparation.

BRIEF DESCRIPTION OF THE DRAWINGS

FIG. 5 illustrates side 1 of a sample treatment chart;

FIG. 6 illustrates side 2 of a sample treatment chart;

FIG. 16 is a sample note print format;

DESCRIPTION OF THE PREFERRED EMBODIMENT

Figure 1:
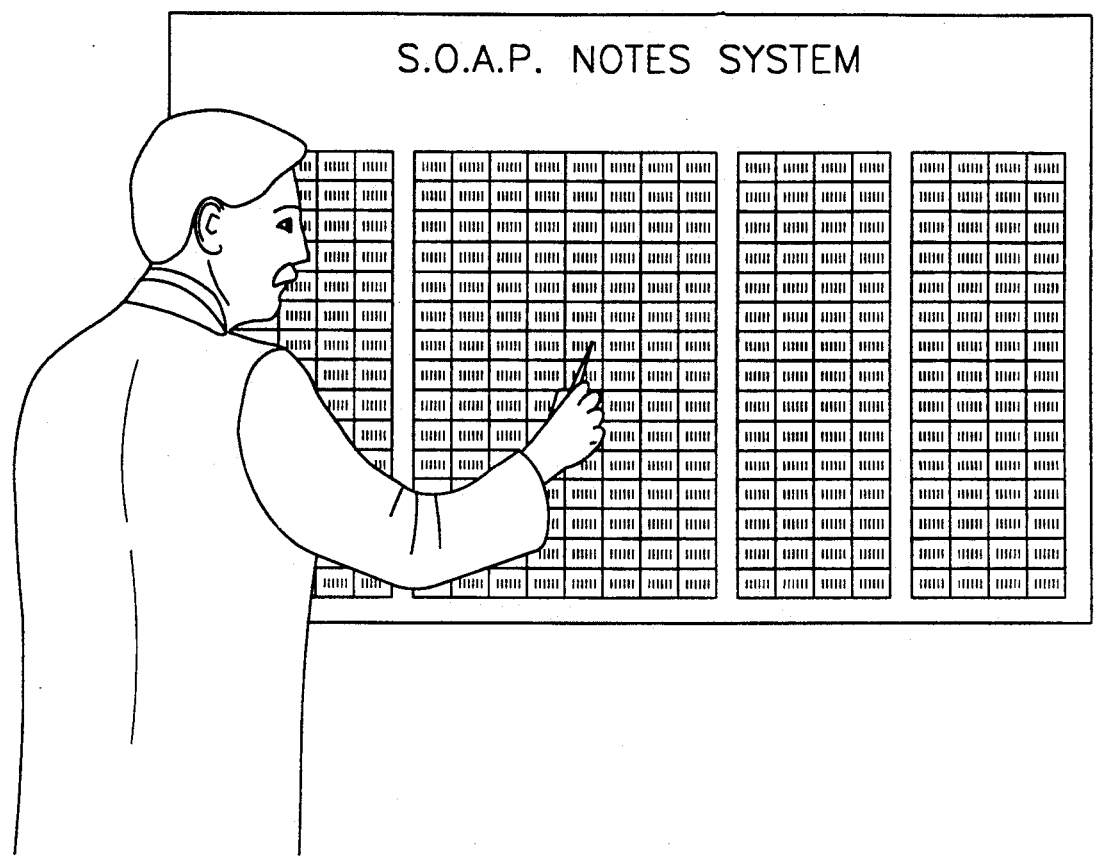
FIG. 1 shows a practitioner scanning bar coded input data arranged on a wall chart.

The apparatus and method for recording progress notes, according to the invention, are described in connection with the embodiment illustrated in FIGS. 1-4 wherein a user or practitioner 10 is shown scanning a bar code 12 on a wall chart bar code input data source 14 with a portable scanning wand 16. The wand stores the scanned codes 12 until such time as the information is to be downloaded into a computer 18 through a recharger/downloader 20. The computer is programmed to compile and edit the scanned bar codes for generating full text progress notes, in complete sentences, of the preassigned input information indicated by the scanned bar codes 12. The computer is connected to a printer 22 for generating printed copies of the progress reports.

The wall chart 14, illustrated in FIG. 1, is specifically designed for the preparation of progress reports in connection with a medical practice, and more precisely, a chiropractic practice. This chart displays literally hundreds of bar codes corresponding to various aspects of a patient examination and treatment. Referring to the wall chart 14, a left zone 22 displays bar codes which each correspond to a subjective symptom that a patient may be complaining of upon entering the office. Another zone 24 displays numerous bar codes corresponding to treatment objectives while a third zone 26 displays bar codes corresponding to the doctor's assessment of the treatment and, finally, a fourth zone 28 displays numerous bar codes corresponding to various options for a continued treatment plan for the patient.

Immediately adjacent each bar code 12 is a mnemonic which is an abbreviated representation of the preassigned input information for that particular bar code. Included herein as "Table 1," prior to the claims, is a listing of the bar codes and associated descriptive text for the bar codes 12 of the wall chart 14 of FIG. 1.

The wall chart 14 is preferably mounted right on the wall in the examining rooms so that, after examining and treating a patient, the chiropractor need only remove his wand from his pocket and first direct it across the bar code on a patients chart to identify a particular patient. The wand scans across the applicable information in each of the various zones 22, 24, 26, and 28. The wand is then scanned across an "accept" bar code 30 on the lower right hand corner of the chart to terminate the notes for that patient. Approximately ninety patients seen throughout a day can be electronically stored in the wand prior to down loading.

"Downloading" simply involves insertion of the wand into the appropriate top slot of the recharger-downloader 20 and punching three keys on the keyboard of the computer 18 where upon all information for up to approximately 90 patients is transferred to the computer memory approximately 2.5 minutes. Those notes can simply be electronically stored and called up on the CRT screen for a particular patient whenever desired or they may be printed for placement in the patient's file.

Whereas the symptoms, objectives, assessment, and treatment plans are arranged on the chart and abbreviated in summary fashion, the software of the system is designed to print out the notes in complete English sentences, adding articles, verbs, and punctuation where appropriate so that the printed progress notes read as if dictated in narrative by the practitioner.

Figure 2:
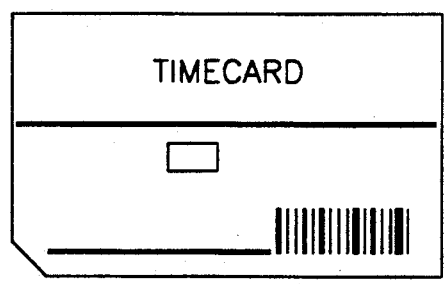
FIG. 2 is a perspective view of a hand-held portable bar code reader or wand.

The wand 16 is illustrated in FIG. 2 as a portable credit card sized bar code reader of the type manufactured by VIDEX under the trademark TIMEWAND. The TIMEWAND is small enough to be carried in a pocket yet powerful enough to hold 2000 scans.

The TIMEWAND has only two features, the corner 32 which scans the code and a button 34 which tells the TIMEWAND to begin.

Since the TIMEWAND is a contact bar code reader, it must come in contact with the bar code. However, the contact should only be enough to lightly drag the read head across the bar code. The TIMEWAND includes rechargeable NI-CAD batteries. For optimum battery performance, the scan button 34 should be released between scans. When not in use, it is recommended to recharge the wand once a month.

Figure 3:
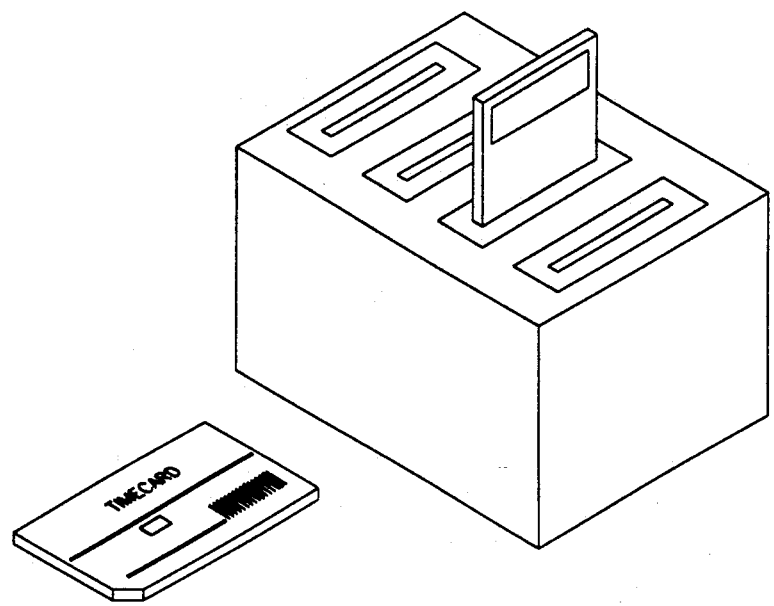
FIG. 3 is a perspective view of the wand recharger/downloader unit.
Figure 4:
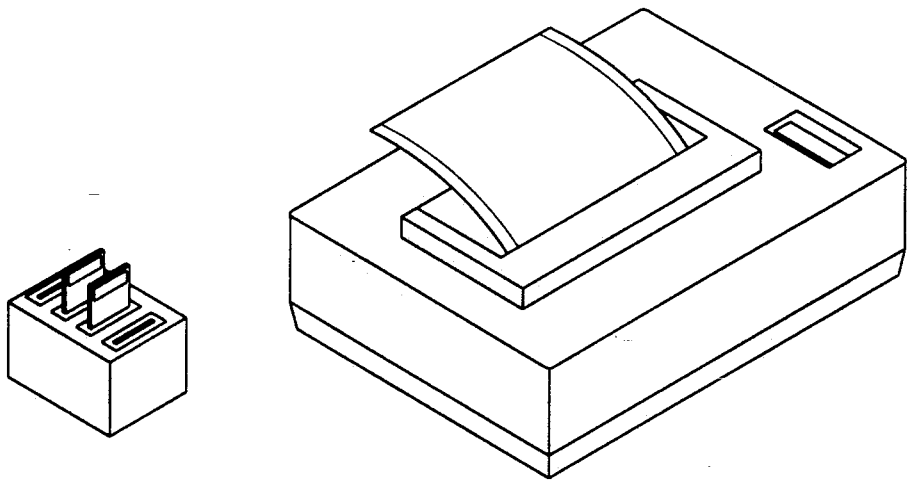
FIG. 4 is a perspective view of the report generating apparatus of the invention.

The TIMEWAND stand or recharger-downloader 20 is shown in FIG. 3 as having a pair of top slots 36 and 38. Front slot 36 receives the wand 16 for recharging it, and back slot 38 receives the wand for downloading data therefrom into the computer memory. The downloader 20 provides the communication link to the office computer 18.

To connect the downloader 20 to the computer 18, the downloader has an output cable 40 with a standard RS232C connector adapted for connection to either the COM1 or COM2 serial port on the back of an IBM computer 18. The other end of this cable is connected to the downloader 20 into the connector marked "T2 Computer." The associated Transformer 42 is plugged into a convenient 110 volt outlet, with the other end of the transformer cable plugged into the center connector on the back of the downloader 20.

Note that the preferred system of the invention requires IBM compatible computer 18 with a minimum of 512 kilobytes of random access memory and DOS 3.1 or greater. A hard disk drive is also required as the data base will rapidly grow making the use of dual floppy disk drives difficult.

Appendix A is the actual RBASE code for the C__ SOAP of the system software.

The following materials in the specification are taken from the operator's manual for the SOAP Notes system and provide much of the operating information for the system. While much of the following is somewhat informal, the manufacture and use of a majority of procedures hereafter disclosed will be apparent to those skilled in the art. Included are references to accompanying figures, tables and appendices.

MAIN MENU

Figures 12, 13:
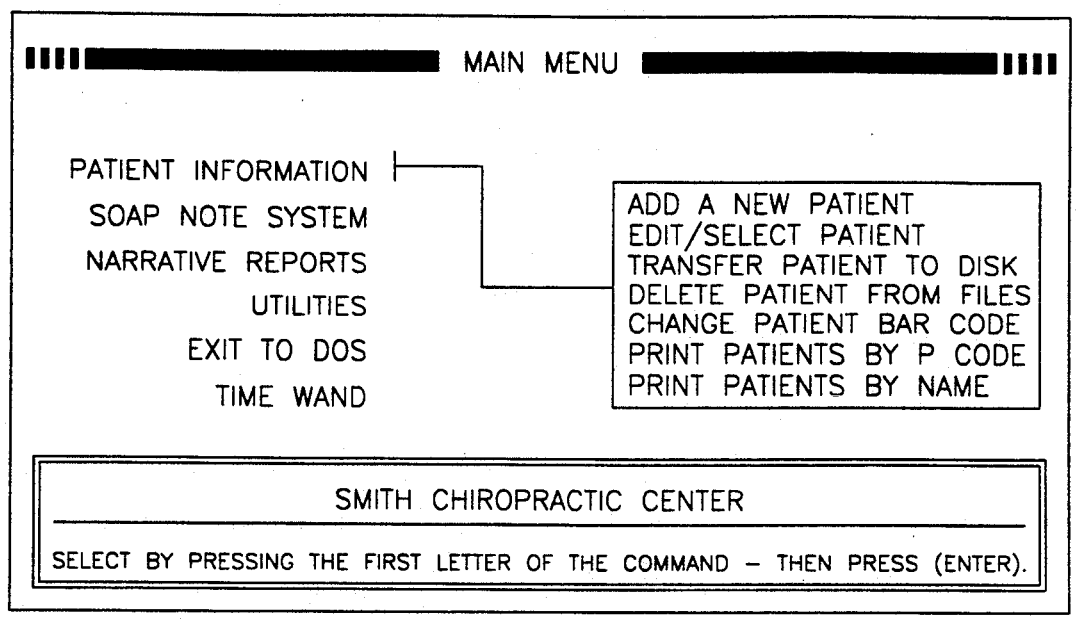
FIG. 12 is a screen display of the main menu of the S.O.A.P. Notes program and the commands available if the "Patient Information" option is chosen.
FIG. 13 is a sample print format for patient information.

Shown in FIG. 12 is tho main menu you see when the SOAP Notes program is run. From here each of the submenus are chosen. Your software has been customized for your clinic. The software and the TimeWand are matched. Now notice that in the menus are several constant items throughout SOAP Notes. First the solid bar at the top of the screen tells you which menu or submenu you are at. By pressing [ESC] you can move back one level of menus. The center portion of the screen is the action area and indicates the choices available. You can pick a choice by the first letter of the name, i.e., PATIENT INFORMATION will be chosen with the command P [ENTER]. The bottom box shows your status at the time and give help for keystrokes.

The box at the right gives you a preview of the submenu choices, i.e., under the main menu choice of PATIENT INFORMATION you will find the areas to ADD a New Patient, EDIT/Select Patient Information, TRANSFER patient to disk, DELETE patient From Files, CHANGE patient Bar Codes and two choices on Printing a list of your patients.

Figure 7:
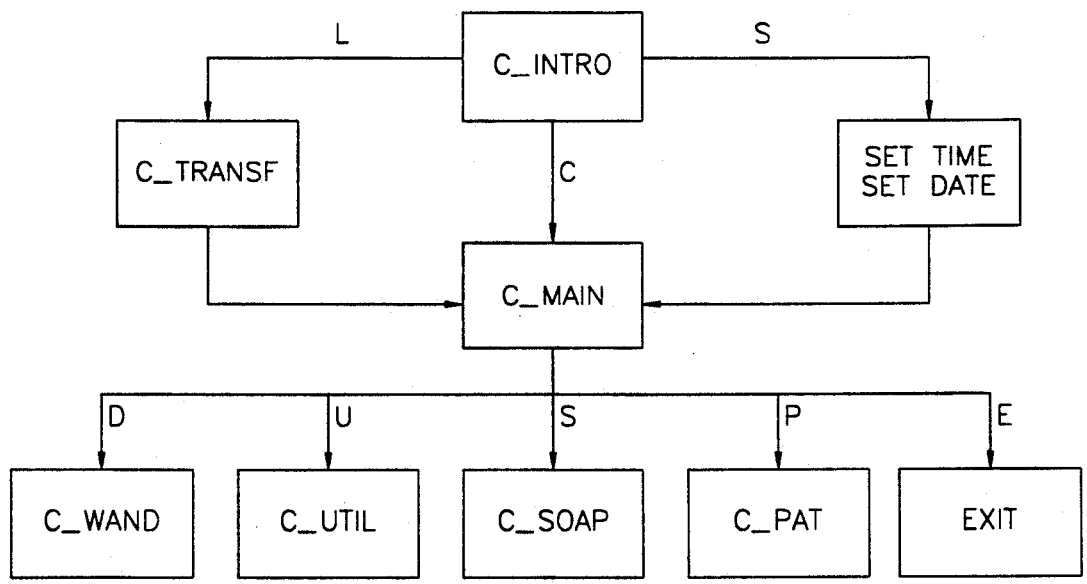
FIG. 7 is a file organization chart of the report generating software of the invention.

FIG. 7 is a file organization chart of the introduction and main software system routines.

Patient Submenu

This is a submenu, its format is constant throughout SOAP Notes.

This submenu displays the choices under the heading of PATIENT INFORMATION. All of the available choices are displayed. To make a choice from a submenu you can either choose the item with the appropriate number (i.e., 1 thru 7) or you can use either the arrow keys or the space bar to move down and highlight your choice. Once you have highlighted hit the [ENTER] key to move on.

One additional item is the use of [ESC] which will take you back one menu from wherever you are. In this case [ESC] would return you to the main menu.

All of the choices under the heading of PATIENT are intended to track your patient lists. The SOAP Notes and visits are tied to the patient files by the use of the patient bar code you assign each patient.

Enough said. Now get several patient charts and proceed to ADD New Patient where you will register the patients into the system.

Figure 8:
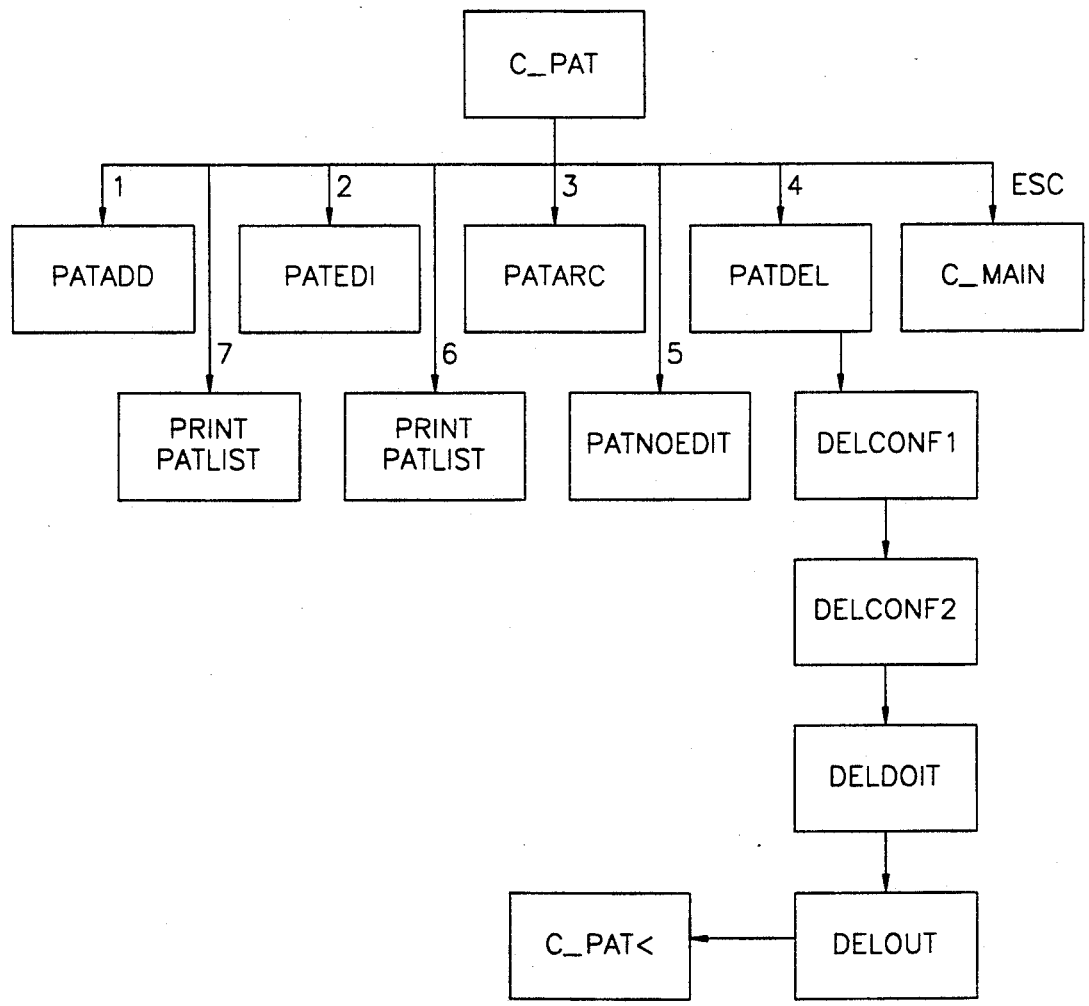
FIG. 8 is a file organization chart of the C_PAT routine of the system software.

FIG. 8 is the file organization chart of the C-PAT routine.

ADD a New Patient

This screen is used to add patients to your database. Each patient needs to be assigned a bar code beginning with "P" from those enclosed in this package. The number of patients and the number of visits the database will hold is limited only by your hard disk storage area. SOAP Notes is designed to use approximately 10 megabytes of memory for 25,000 patient visits. This will depend of course on your level of verbosity and to the extent you choose to use the free text SOAP Notes option.

Try adding one of your patients now. Put your [CAPS LOCK] key on first. The file bar needs to be exactly as on the sticker which you will place on the patient's permanent record including the "P" i.e. P00000123. The second field is for the patient ID number or any patient number assigned by your office. This is to maintain consistency with your current system. Now enter the patient's last name and first name. Notice the bottom box which simulates a mailing label. The last name and first name will appear below. Add a one line address for the patient and press [ENTER]. Now add the city, the state and the zip each separated by an [ENTER]. Your cursor should move to the Group field for you to enter the code assigned by your office to identify classes of insurance. To add new groups see the Utilities section of this manual. After the Group code you are given a help menu which allows you to Add the patient, edit the data, discard the data or enter another patient. Highlight your choice and press [ENTER].

Don't worry if you make a mistake, you can either edit it later or return to the input form field by using [SHIFT] [TAB] at the same time. Notice also that the [BACKSPACE] key will remove letters one at a time. You can jump forward one field at a time with the [TAB] key.

[ADD a New Patient]

There. You have finished adding your first patient to the database. Whenever you scan the number P0000333 (or whichever patient bar code you used), the SOAP Notes program will link the information to this patient.

Edit Patient Information

This submenu feature allows you to modify the patient information in the case of name changes, address changes or changes in your own patient ID number. Because the patient Bar Code is used to link all of one patient's visits and notes together, to change the patient Bar Code is a separate function under this same menu.

Once you enter this Option you will see a submenu which allows you to more quickly find the patient you wish to edit. This may not seem important now but as your SOAP Notes database grows with hundreds of patients you will find it increasingly useful.

Notice the options to find the patient you wish to edit. Option (1) is to find your patient if you know the exact last name. The first initial is actually optional, but will limit your choices in a large patient database. Option (2) is provided when you know only a portion of the patient's last name. If you wish to find the patients with the last name of "Hamilton" or "Hambleton" you can enter HAM*. Notice the asterisk. This tells the SOAP Notes Database to show you every person whose last name begins with HAM followed by any number of other letters. The more you know of the name the smaller your search of patients will be. Imagine a large practice using SOAP Notes and you only knew the patient's name began with an "S*". Option (3) allows you to find a patient based on the Scan Code from the patient's treatment card. This is the quickest way and assumes you know the patient Bar Code. Option (4) allows you to find a patient when you know the patient account number assigned by your office.

Once you have entered the name or the number of a patient, you are given an edit form identical to the ADD Patient input form. Try each of these options on the patients you entered before. See how easy it is to change patient information. The help menu which appears at the bottom allows you to either accept your changes, discard your changes or edit several patients in a group.

EDIT/Select Patient File

Another feature of the Edit Option allows you to page through your selected patients. To see the next alphabetical patient use the [F8] key or to see the previous patient use the [F7] key. This way you don't have to return to the main menu to find a patient close to the one you chose to edit.

After you finish editing the patient data, use the [ESC] key to return to the menu.

TRANSFER PATIENT TO DISK

This feature has been included for your future decisions. If you wish to limit the growth size of your database, patients which are no longer current can be archived to a floppy disk for later retrieval. This option is also used *before* you delete patients from the database just in case you would later decide to add the patient back in. This could occur in our mobile society as people move in and out of your area or switch between chiropractors.

The TRANSFER option is like the utilities option of Archive and Restore but in this case only one patient will be removed from the database to a floppy disk.

The TRANSFER procedure is straightforward. You are first asked whether you wish to Archive (Transfer patient file to floppy disk) or to Restore (Copy patient file from floppy disk). Place a formatted floppy disk in drive A: of your computer and press [ENTER].

Transfer a Patient to a Floppy Disk

This menu allows you to choose which drive to transfer the patient data to. As there are many types of computers and configurations, this may be confusing. Most floppy disks are either assigned to Drive A: or Drive B:. If you don't know which, choose A:.

The choices of C:, D: and E: allow you to transfer the patient to either another area of your hard disk or possibly to a tape backup system.

DELETE Patient from Files

WARNING Be certain that you have transferred this patient data to a floppy disk before you delete the patient. Once a patient is deleted the patient visits and their associated SOAP Notes cannot be retrieved if you do not have a copy on a floppy disk.

The delete feature allows you to search for the patient in the manner you have previously learned. After you choose the patient to delete, it will verify twice that you wish to delete the patient. After the second chance, all the patient information of your choice is erased from the hard disk. This includes all the visits of that patient.

CHANGE PATIENT FILE P BAR CODE NUMBER

This is a simple edit option to change the patient Bar Code Number that a patient is assigned. SOAP Notes includes a set of 3 similar bar codes. Some chiropractors may fill more than three patient cards and may require more than 3 of the patient Bar Codes. You can then assign to the patient a new patient bar code and all previous visits will be marked appropriately so they are still linked to the new patient bar code. This option does not edit the Patient Account Number which can be done with the EDIT/Select Patient above.

Also, if a patient should accidentally be assigned two numbers, this option will simply copy the codes to a new fresh number. It will maintain the visit date, physician and all pertinent information.

PRINT PATIENT LISTS

This option is the easiest to use. You pick the item from the menu and your printer does the rest. It will print an alphabetical list of the patients you have entered into the system. On the list is the patient Account Number and the Patient scan code for your reference. The addresses in the system are also printed.

You may also choose to print a list sorted by patient Bar Code Number.

FIG. 13 shows a preferred printing format upon activation of this option.

SOAP NOTES SYSTEM

Figure 14:
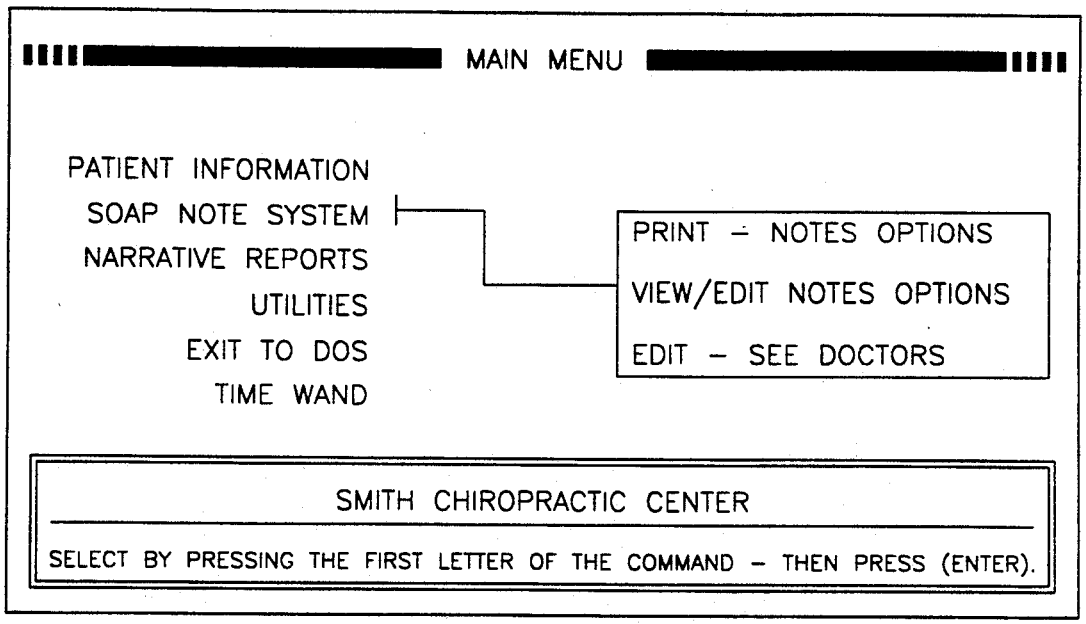
FIG. 14 is a screen display of the main menu and the commands available if the "S.O.A.P. Note System" option is chosen.

Shown in FIG. 14 are the options available under the SOAP Notes System option, which is the heart of the SOAP Notes program. In this module you will find the functions to print, view and edit the SOAP Notes. You will be able to enter free text and list the cases which you flagged as "SEE DOCTOR".

The "SEE DOCTOR" option exists because we know that every situation cannot be described by the SOAP Notes chart. Many times you will start to scan the codes to describe a patient visit and find that in that particular case, you prefer to dictate your own set of notes. This is an option provided. At your convenience, you may ask the computer for a list of all patients who need additional SOAP Notes information added.

Several methods to print the notes are provided. In creating the SOAP Notes system we tried to follow the rules of English and add punctuation, conjunctives and conjunctive phrases where appropriate. This slows viewing of the notes especially for those of you with XT class computers. As a result we developed a speed printing option, where we relaxed these rules of English to quickly give you patient notes. Try each method and use that which you prefer. You will find SOAP Notes a singular product with unique features aimed at providing you, the chiropractor, with a productivity tool like no other. The printing options and speed are discussed later in this manual.

Figure 9:
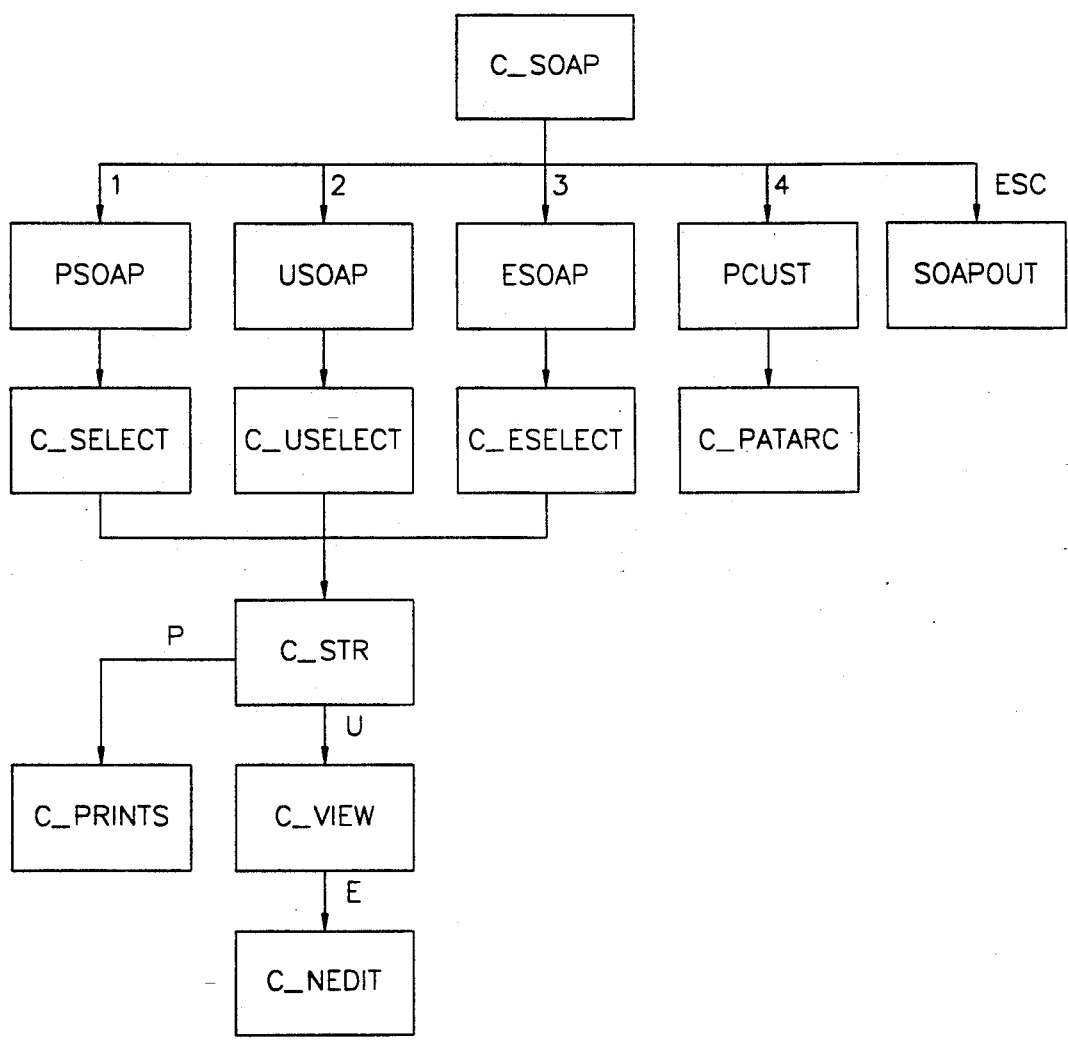
FIG. 9 is a file organization chart of the C_SOAP routine of the system software.

FIG. 9 is a file organization chart of the C-SOAP routine.

PRINT—NOTES OPTIONS

Your choices are to print a single patient with a range of dates or to print the SOAP Notes on each of the patients you saw during a range of dates. When you choose this option your computer will find the bar codes you scanned for the patient. It will substitute English text for each bar code. If you want a single visit or to print notes for a single day, then the starting date and ending date of that range will be the same day.

Print all Patient Notes (Date Range). In clinics where they print the patients out for the entire day this will be utilized the most frequently. Your first option is to print patients by groups. You then supply the date range and whether you want to use continuous form paper or pressure sensitive labels. The system is designed for 1"×8½" labels.

One Patient Notes (Date Range). This feature allows you to retrieve one patient's case notes for any date range you choose. When you select the patient Group code you will only print that particular group. In order to print all patients regardless of group code you need only to press [ENTER].

The date range format is given, but any delineator will work as long as the date is in the format of MM-DD-YY. We provided the "/" delineator as an example only.

The computer repeats your choices and asks in which order you wish the patient's sorted, either ascending date (earliest first) or descending date (most recent first). You may also cancel the print at this point.

Figure 15:
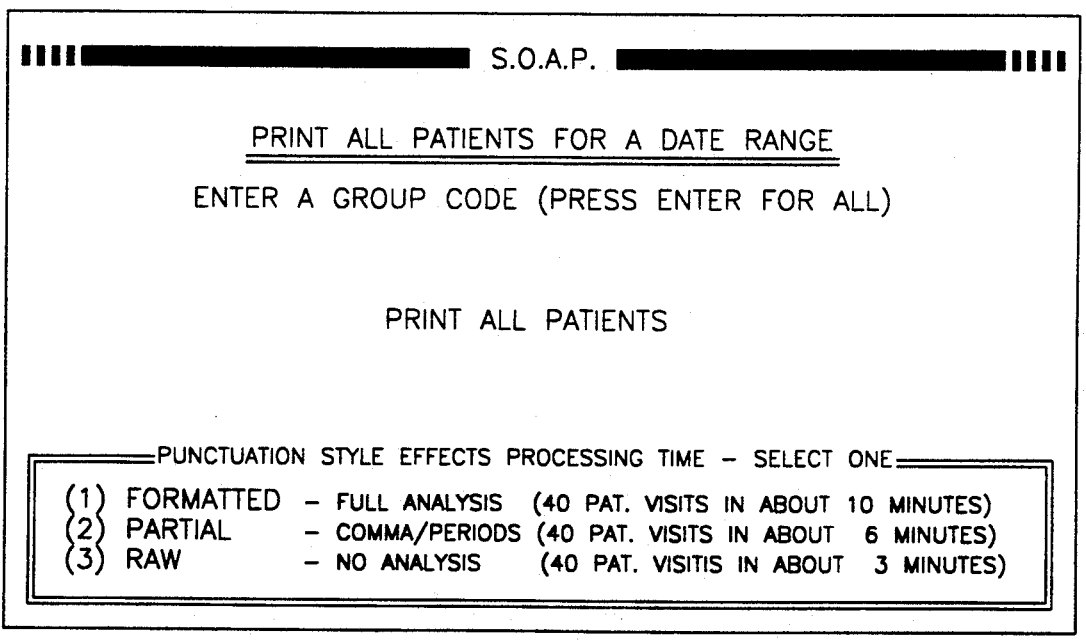
FIG. 15 is a screen display showing the choices available for printing notes and estimated times therefor.

When choosing the Punctuation Style you will find that the more correct the English and punctuation, the longer the processing time. This is especially true if you have chosen 40 or more patients to print. The times shown in FIG. 15 are estimates of what would be seen on an average AT class computer. If you have an XT class machine, they will be longer, if you have an 80386 machine they will be much shorter.

This is also true with the approximate time to completion. There are far too many types of machines for this to be exact, but this provides an approximation for you while the machine processes the SOAP Notes.

When you choose to print on pressure sensitive labels the compute will prompt you to check alignment. The system is designed to print on 2-inch continuous feed labels. Make certain the X's printed on the "test print" are at the very top of the label. If you are now using 1-inch labels you will notice that the printer may skip a label as it resets to the top of the next label.

The last option is for those people whose office system can accept an ASCII file for word processing. Instead of printing your reports to the printer it allows you to print to a file. It will create a file called DATE-Hour.Minute (i.e. Apr1310:52 was printed on April 13th at 10:52 a.m.). This file is created in the same directory as your SOAP Notes file system. The purpose of naming it after the date and time is so that subsequent prints of the file do not overwrite each other. Be alert that if you use this option often you will need to delete all these ASCII files periodically or you will fill your hard disk up fast!

VIEW—NOTES OPTIONS

When you choose to view a single patient the computer will step back through each visit. The only item you need to input is the patient Bar Code number for the patient, a single patient or to view the last SOAP Notes on a patient. When you choose this option your computer will find the bar codes you scanned for the patient.

It will substitute the English text for each bar code. Finally the computer will add the conjunctives and punctuation to make the text readable.

The SOAP Notes program will next ask you to enter the Starting Date you wish to see. Only one date is entered as you can step backwards through prior visits of the patient from this point. After the first visit is displayed, you see the options to view the Next visit, the Previous visit, to edit the SOAP Notes or to quit viewing the Patient visits.

EDIT NOTES OPTION

The above option lets you page through the notes on the selected patient. You can delete an individual note by choosing the "D" choice. The computer will ask you to confirm that you really intend to delete this note. Both "N" and "P" display the following and previous notes. The "Q" choice returns you to the menu to select another patient for viewing.

The major function is to edit a note. By choosing "E" you are placed into a free text field showing your note.

EDIT NOTES OPTION

Your previous note is shown within a double line box, just as you scanned it in. It has been converted from codes into text. You can now edit the note and type in anything you wish. The note will be stored as you have typed it and the old scans are deleted.

The edit mode was not intended to be a word processor. It is a very simple editor. You can use the [DELETE] key to delete, the [INSERT] key to insert, and you can move about the note with the arrow keys, the [SPACE] bar, [HOME] and [END]. After you have the note as you wish it, press [ESC] to file the note.

EDIT TIME FOLLOWING EDIT OF NOTE

Above this patient is the scan date. We found that often the physician's office personnel were changing their computer date and time. This was also true of some older computers which did not have an internal clock to keep date and time. In these cases the date on the SOAP Notes was wrong. At the end of each download process, the computer resets the date and time clock in the TimeWand. If the computer was wrong, the TimeWand will now be wrong. If you need to reset the clock in the TimeWand you can download the empty TimeWand just to reset the clock.

To alleviate this we have a function to edit the date and time on each note after you edit. Answering this question with a "Y" places the cursor at the date field in the top box so that you can change the date. After you finish, press [ESC] to save the changed date.

EDIT—SEE DOCTOR

When the physician scans the bar code "SEE DOCTOR" the SOAP Notes system gives you the option to print a review form of these cases for later review. It is assumed that in these cases he or she would choose to dictate the patient notes. If the physician chooses, space is provided to hand write the patient notes as well. The first option prints a review form of each case in the system which includes the bar code for "SEE DOCTOR". As each of these cases is resolved, it will be removed from this form on subsequent printings.

A preferred format for this output is shown in FIG. 16.

After the physician has dictated the patient notes, the system uses the same editing method you have learned to step through each case on the review forms for your editing via bar codes or by entering free text.

UTILITIES SUBMENU

Figure 17:
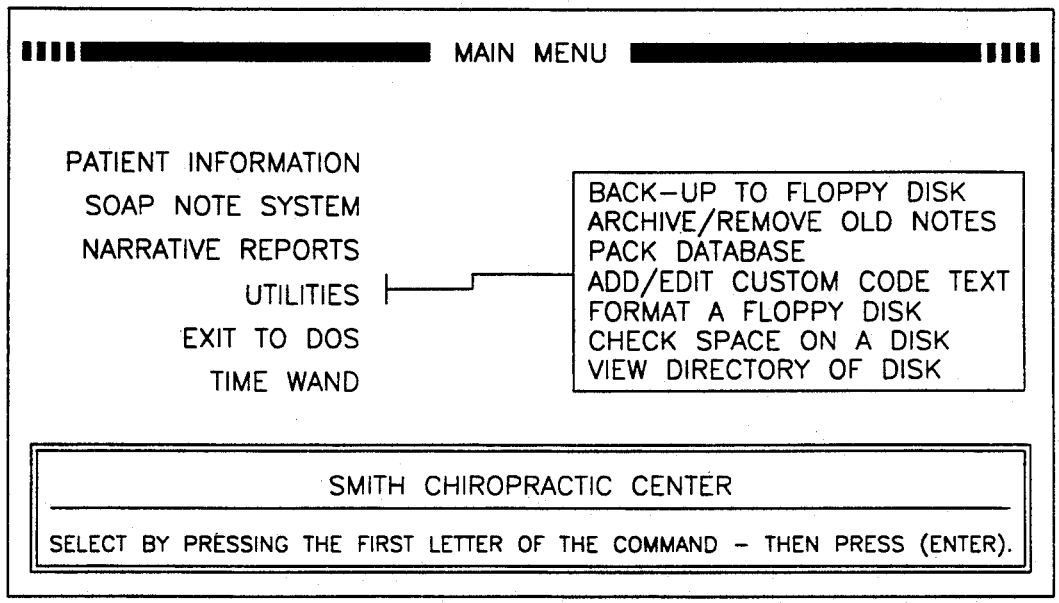
FIG. 17 is a screen display of the main menu and the commands available if the "Utilities" option is chosen.

These utilities, as shown in FIG. 17, are written to provide you with the tools to continue to use your new SOAP Notes system for years. As you see more and more patients, the database will grow. Some people feel that they will simply purchase a larger hard disk, while other chiropractic clinics will choose to archive old notes and keep only the most current cases "on-line". Other features allow you to rebuild (Pack) your database to get the most efficient use of your hard disk space. The most important feature of the utilities is the backup system. You must do backups on your date. It is important to your practice and patients to maintain their data.

Figure 10:
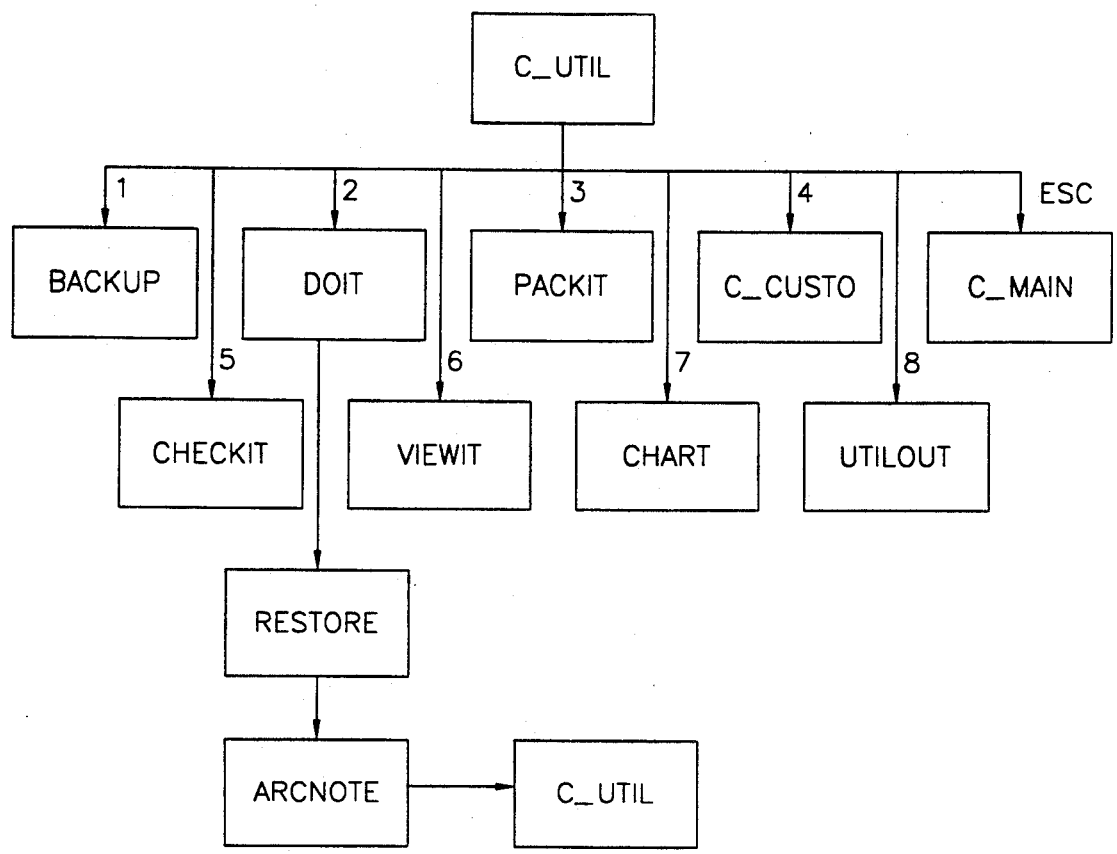
FIG. 10 is a file organization chart of the C_SOAP routine of the system software.

FIG. 10 is a file organization chart of the C-UTIL routine.

BACK-UP to Floppy Disk

Custom Applications Development Co. cannot be responsible for your data. Assume your hard disk is going to fail at some time. This is not to scare you off, it is a statement of fact.

Now that we have your attention we will discuss backup. SOAP Notes has a backup feature to make a backup copy of your patient database to FORMATTED floppy disks. Floppy disks hold either 360K (XT machines) or 1.2 meg (AT machines). You will need to have formatted floppy disks prior to using this procedure.

We recommend daily backups. Our recommendation is to have three separate sets of backup disks which you rotate on a daily basis. Follow this scheme. Mark the first set red, the second set blue and the third set yellow. On Monday, backup using the red set, Tuesday backup to the blue set and Wednesday backup to the yellow set. Thursday you reuse the red set and Friday you reuse the blue set. This may seem over cautious but it will ensure that you at least have one good set of backup disks. A very handy option is the new tape backup systems which can be purchased for less than $500. These will backup a 40 meg hard disk to tape in 17 minutes. The procedure is straightforward. The computer will tell you to insert the first disk, when to change disks, etc.

ARCHIVE/RESTORE OLD NOTES

This feature has been added for your future use. As the database grows you may find that your hard disk is too small for all the patient visits. This may especially be true if you have many other programs on the same hard disk.

In order to archive you need to select a date. All patient notes and visit information prior to this date will be stored on floppy disks. You can restore this information at a later time if you choose.

The procedure first asks if you intend to Archive or Restore. Choose one with either "A" for archive or "R" for restore. The next screen will give you a warning. The patients you archive are deleted from your hard disk. You will then be prompted for a date. An example would be to choose Dec. 1, 1988 and all patient visits prior to and including that day will be copied to a floppy disk. In the case of both Archive and Restore, the disk messages are intended for larger amounts of data. If you Archive many patients the messages to change disks are appropriate. You would want to fill up one floppy disk, then another and so on. If on the other hand you choose to only Archive a few patients the messages are somewhat redundant. It will tell you three times to put in the next disk. If you have only one disk and a few patients to archive it will work to keep using the same disk over.

Select the Drive or Floppy Disk

This menu allows you to choose which drive to transfer the patient data to. As there are many types of computers and configurations this may be confusing. Most floppy disks are either assigned to Drive A: or Drive B:. If you don't know which, choose A:.

The choices of C:, D: and E: allow you to transfer the patient to either another area of your hard disk or possibly to a tape backup system.

PACK DATABASE

As you add and delete patients and notes over time, the database gathers extra unused space. To recapture this space SOAP Notes has a feature called Pack. Packing is an automatic procedure that may take quite some time depending on the size of your database. Do not interrupt the pack procedure. It may take several hours in a very large database which has many unused sections of leftover garbage. Don't become alarmed, allow the computer to reorganized your database and you will be surprised at the space savings and how much more quickly information is found.

The database is like a tree with many branches. So much, in fact, we call the data file a B-tree. As you add data it grows taller. The more branches, the longer the path to your information. By packing the database the tree becomes "bushy" or less tall. Fewer branches make a more direct path to your data.

ADDING YOUR OWN CUSTOM SOAP NOTES

On your SOAP Notes chart are many empty scan codes. These are for phrases which you routinely use. The phrase can be up to 70 characters in length including punctuation. The SOAP Notes chart is laminated so you can write a mnemonic on the chart to remind yourself which phrase the code will produce.

Figure 6:
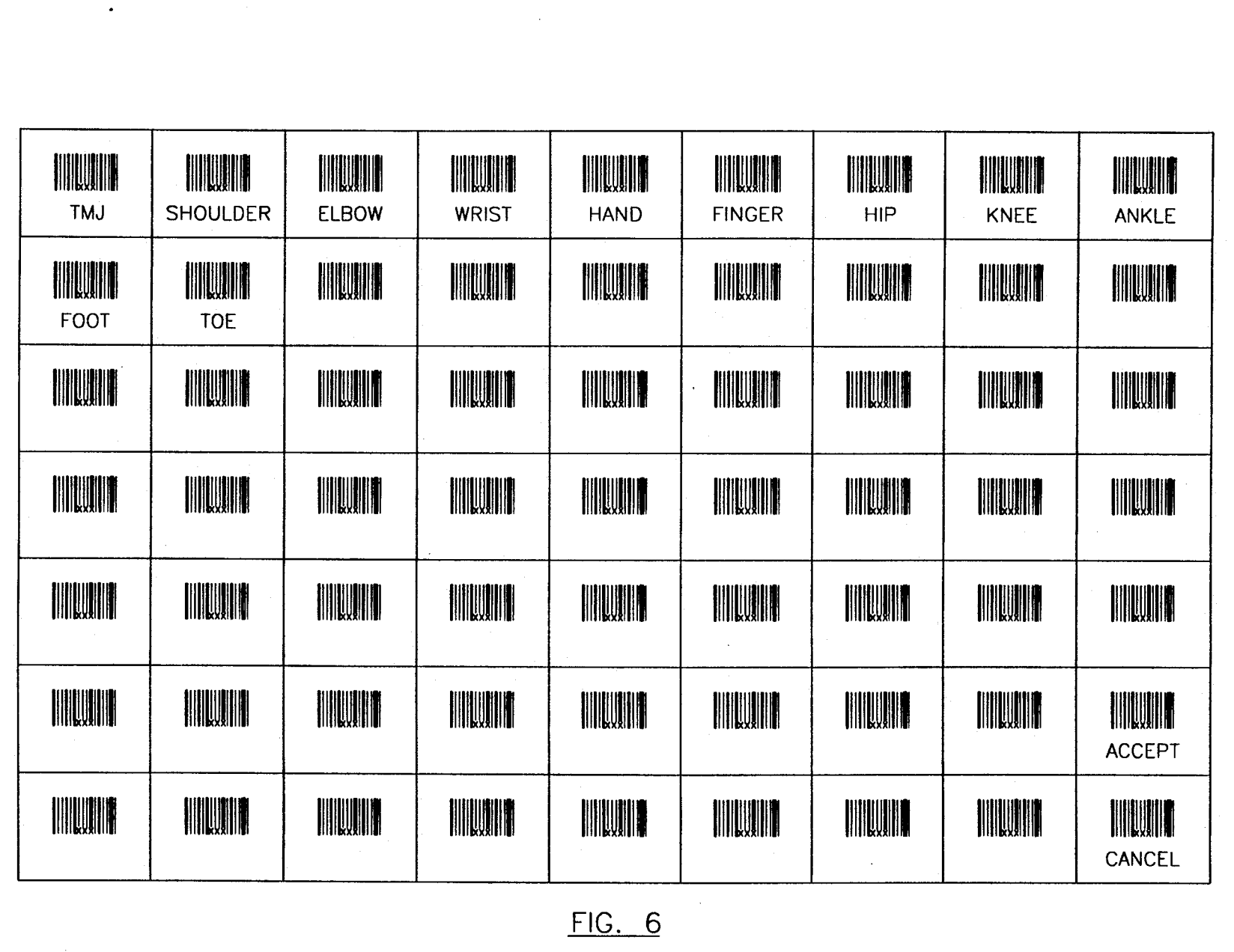

Take a moment to review the layout of the chart shown in FIGS. 5 and 6. On the top row are phrases which begin sentences in their respective categories. Following this are modifiers (adjectives) in the light blue area. Next are subcategories for the parts of the anatomy, diagnosis and your treatment plan. Each subcategory has empty codes which are intended for you to assign. These are the phrases you currently use daily.

The add Custom SOAP Notes is the feature of our system that makes it unique to your office.

When you assign a Custom SOAP Notes code you first write on the chart a mnemonic phrase to remind yourself. Then you may choose to hand write that phrase in the list of codes at the back of this manual. Last, tell the computer what code you have assigned to which phrase.

In this utility option enter the code first. The computer responds by telling you in which subcategory the code belongs and gives you instructions how to enter the phrase. Type the phrase exactly as you want it to print.

At the bottom of the chart is a wide band of rows in which the codes do not have a subcategory. In this area you may insert full length sentences. The SOAP Notes program will not process this text, only add a period in the right place. Each of these special codes can be assigned to a complete sentence of up to 70 characters in length. You may choose to use several codes consecutively to give a full thought to the patient notes, but you must then remember to scan those codes in the same order you choose.

FORMAT A FLOPPY DISK

In order to write information on a floppy disk it must be formatted. This causes more questions form first time users: Why? A floppy disk is like any recording media. In order for your disk drive to read information from the disk or write to the disk, it needs to set up a pattern. Like the musical records we are all familiar with have a track, so a floppy disk has a pattern in which information is read. It also needs to have a directory set up of the files you wish to place on the disk. This directory is read only by the disk drive and is called a File Allocation Table. Formatting a floppy disk sets up this File Allocation Table on the disk.

Your computer knows how to format a floppy disk. What you need to have is the proper size diskettes for your drive. An AT system uses 1.2 meg floppy disks labeled DS/HD while an XT system uses 360K disks labeled DS/DD. They are not interchangeable. We also are asked often what type of disks to buy and we always reply that only three manufacturers make the actual media but hundreds of vendors make the cardboard covers. Any standard quality disk will suffice.

The procedure is straightforward. Put the disk in the drive you choose and the computer does the rest.

CHECK SPACE ON A DISK

View Directory of a Disk

These two standard DOS features were added here so you could check how much space the SOAP Notes program was using. Periodically assure yourself that your program has enough disk space to file the day's work.

WARNING . . . Running out of disk storage space during some phases of any database maintenance could cause damage to the database. This is true of all database programs, not just SOAP Notes. If you find that you have less than 1 meg (1024K) of free disk space, you need to make a decision to purchase more storage space or to free up some space on your hard disk. Either remove redundant files or use our ARCHIVE system to move older patient visits "off-line" to a floppy disk.

EDIT OR ADD GROUP CODES

This option allows you to identify and sort patients by classes, i.e. Medicare, Insurance, Worker's Compensation or whatever. This is a list of Group Codes to which you can add/delete or edit as you choose. By marking patients with a group code, in the Print Patient List option you will see a choice to print sorted by group code.

SET THE DEFAULT PRINTER PORT

This option allows you to set which port your printer is assigned to. If you do not know the answer, use the setting of LPT1. This is the DOS standard location.

TIME WAND OPTIONS

Figure 18:
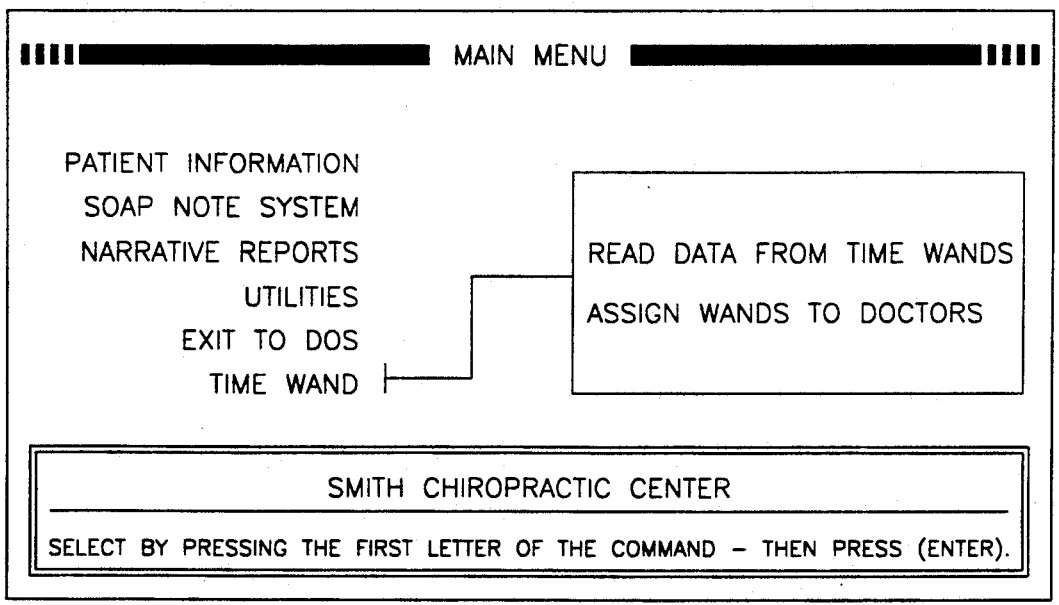
FIG. 18 is a screen display of the main menu and the commands available if the "Time Wand" option is chosen.

There are only two TimeWand options, as shown in FIG. 18. The first is to move information from the TimeWand to your computer. Place the TimeWand into the RECHARGER and press the Scan button. When you choose the option to READ DATA from TimeWand, the computer will automatically begin to transfer the information stored in the TimeWand. Follow the instructions on the next page very carefully. It is important that you remember to press the Scan Code button each time you place the wand in the RECHARGER. This allows the battery to fully charge.

The other option lets the TimeWand know which physician is using which wand. In a large practice, the patient visits are marked by physician only when this is kept current. WARNING . . . If Doctor Smith uses the wand, followed by Dr. Jones, and you have not reassigned the TimeWand, the patients that Dr. Jones sees will be marked as seen by Dr. Smith in the SOAP Notes program.

Figure 11:
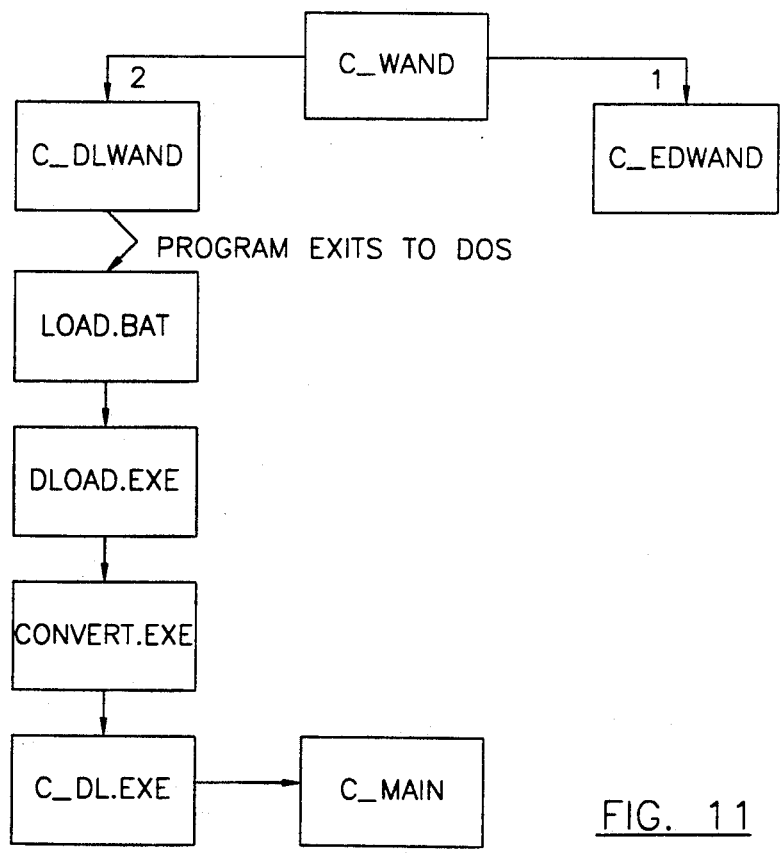
FIG. 11 is a file organization chart of C_WAND routine of the system software.

FIG. 11 is a file organization chart of the C-WAND routine.

Place the TimeWands in their chargers. Press the button on one of the wands. When they are securely seated, press the [SPACE] bar on the keyboard. Watch the lights blinking on the TimeWand charger unit. When you notice that only the RECEIVE light is blinking, and that the wands are no longer making sounds, then press the [SPACE] bar on the keyboard again.

READ DATA FROM THE TIMEWAND

This routine allows you to move the data you have scanned from the TimeWand into your computer. By selecting this option the computer first copies the raw data from the TimeWand to the computer, then translates that data into your SOAP Notes database. Remember to press the button on the TimeWand when setting it in the RECHARGER. To run the program, press the [SPACE] bar again. The rest is automatic. You can watch the Transmit and Receive lights on the RECHARGER blink and hear the TimeWand click as it sends its information. Once the procedure is finished, only the Receive light will blink, indicating the TimeWand is done transmitting data. Wait until you are sure that all the data has been transmitted before striking the [SPACE] bar again. Failure to wait until the TimeWand is finished could result in the loss of data. In most cases, however, you should be able to retransmit the data should the process be interrupted before it finishes.

If you are downloading information from more than one TimeWand, the wands will send their information to the computer one after the other. Wait until you know that all of your TimeWands have finished sending information before you strike the [SPACE] bar the second time.

ASSIGN WANDS TO DOCTORS

The Doctor's name is carried in each TimeWand in order for the database to know which doctor scanned the data (examined the patient).

The current assignments are first displayed and the computer asks if you wish to change or edit these.

In the lower edit box, each assignment is displayed one at a time. Change either the Doctor or the WandID. The [F7] key goes back one WandID and the [F8] key advances to the next WandID. The [ENTER] key advances step by step from WandID to Doctor to next WandID, etc.

The bottom help menu allows you to save your changes, re-edit the changes or discard the changes.

DOWNLOAD COMPLETE

After the download process is complete, the above message is shown and you are asked if you would like to print a list of patients in the wand before they are written to the database.

On this patient list is the scan time and date. We found that often the physician's office personnel were changing their computer date and time. This was also true of some older computers which did not have an internal clock to keep date and time. In these cases the date and time on the SOAP Notes were wrong. At the end of each download process, the computer resets the date and time clock in the TimeWand. If the computer was wrong, the TimeWand will now be wrong. If you need to reset the clock in the TimeWand you can download the empty TimeWand just to reset the clock.

To alleviate this we have a function to edit the date and time on each note before it is added to your database. We found this was also useful when physicians wanted to go back and scan past notes into the system. You can scan the notes at one setting then edit the date and time prior to writing the notes to the database.

The following description is illustrative of a preferred embodiment of the SOAP Notes program as disclosed in Appendix A.

Referring to Appendix A, which contains the source code for the SOAP Notes software, it is seen that pages 1 and 2 and the upper two-thirds of page 3 set up the various data structures and pointers of the SOAP Notes database. As seen on page 1, lines 17-26, the structure "scodes row storage" is defined, which has three main components: "scode", which represents the bar code on the chart that is scanned, "sdesc", which represents the actual phrase used in combining with other phrases, and "pct", which is a numerical value indicative of phrase type, as also shown in Table 1, column 3. Also included in the "scodes" data structure is "type", which represents the grammatical category to which the phrase in "sdesc" is assigned, such as modifier, adjective, noun, etc., as shown on page 1, line 20. An example of a typical set of data stored in the above described data structure is seen in Table 1, page 1, line 1, where the "scode" is "SAA", the "sdesc" is "constant", the "pct" is "0", and the "type" is "modif" for modifier.

As the separate phrases are put in storage, shown on page 4, line 50 and onward to page 7, line 22, the phrases are stored in note data structures, as explained on page 6, lines 14-18, which are labeled "DICTATE" and "LONG", stored in one or the other according to length (if shorter than 800 characters, store in "DICTATE", otherwise store in "LONG", these figures coming from the data structures as defined on page 1, lines 42-47 and 55-60).

Beginning on page 7, line 65 and continuing to page 12, line 14 are the actual note processing sections of the program. The file "wand.txt" is opened and the first patient code or "pcode" record is found, page 7, line 65 to page 8, line 8. The first "scode" is then found, as shown on page 8, lines 12-14. After a short initialization process, the note may be processed, starting at line 28 of page 8.

The processing begins by locating a bar code in the "Scode" array, page 8, lines 30-35. If no "Scode" is found (line 38), an error message is printed by the phrase "[Invalid Scan Code —]" being inserted into the note (line 40). If the note is too long, another error message is printed by the phrase "NOTE TRUNCATED" being inserted into the note (lines 45-49). A flag, "invalid see doc_flag", is then set to inform the program of either of the above two conditions.

The PCT value corresponding to the bar code is taken from the array. If the PCT value is 7 then, as shown on line 55, no punctuation is needed. If the PCT value is 9, a period is concatenated to the note and the phrase corresponding to the present "Scode" is concatenated to the note following the period, as shown on page 8, lines 56-58 and page 10, lines 12-25.

The bar codes are then read in and stored in variables "process [1]. Scode," "process [2]. Scode" and "process [3]. Scode," page 8, lines 32-35. On page 8, lines 61-65, if the PCT of the bar code equals 10, the "invalid_seedoc_flag" is set for quick review/attention after process. If the PCT value of the third bar code is 0, 7 or 9 no further punctuation is needed, as shown on page 9, lines 7-9. Otherwise the program checks to see if the three bar codes in the buffer have the same PCT values, a comma is concatenated to the note, page 9, lines 15-18. If the PCT values of the second and third are equal but not the first and third the word "and" is inserted between the second and third bar code phrase as shown on page 9, lines 20-22. Finally, if the PCT value of the second bar code is 5, the word "is" is also added, page 9, lines 23 and 24, making the words between the second and third phrases become "and is." Once again the note is checked to make sure that it is not too long (page 9, lines 28-35), and the processing continues until that visit is finished.

On page 10, lines 46 and onward, the final punctuation and storage of the note is accomplished. On line 54, a final period is added if needed. Finally, on page 10, line 57 to page 12, line 14, the storage of all the note and visit data is filed for later retrieval.

As can be seen from the above description, the present invention provides a novel and simple method and apparatus for recording progress notes. Therefore, an apparatus and method has been described and shown which accomplishes at least all of the stated objectives.

TABLE 1

| BARCODES - KEYWORDS - DESCRIPTIVE TEXT | | | |
|---|---|---|---|
| BAR | FULL TEXT | PCT STAT | TYPE |
| SAA | constant | 0 | CHAR MODIF |
| SAB | frequent | 0 | CHAR MODIF |
| SAC | intermittent | 0 | CHAR MODIF |
| SAD | occasional | 0 | CHAR MODIF |
| SAE | insidious | 0 | CHAR MODIF |
| SAF | nerve | 0 | CHAR MODIF |
| SAG | severe | 0 | CHAR MODIF |
| SAH | moderate | 0 | CHAR MODIF |
| SAI | mild | 0 | CHAR MODIF |
| SAJ | acute | 0 | CHAR MODIF |
| SAK | bone | 0 | CHAR MODIF |
| SAL | chronic | 0 | CHAR MODIF |
| SAM | muscle | 0 | CHAR MODIF |
| SAN | upper | 0 | CHAR MODIF |
| SAO | middle | 0 | CHAR MODIF |
| SAP | lower | 0 | CHAR MODIF |
| SAQ | connective tissue | 0 | CHAR MODIF |
| SAR | left | 0 | CHAR MODIF |
| SAS | right | 0 | CHAR MODIF |
| SAT | bilateral | 0 | CHAR MODIF |
| SAU | joint | 0 | CHAR MODIF |
| SAV | anterior | 0 | CHAR MODIF |
| SAW | posterior | 0 | CHAR MODIF |
| SAX | lateral | 0 | CHAR MODIF |
| SAY | medial | 0 | CHAR MODIF |
| SAZ | flexion | 0 | CHAR MODIF |
| SBA | general | 0 | CHAR MODIF |
| SBB | extension | 0 | CHAR MODIF |
| SBC | cervical | 0 | CHAR MODIF |
| SBD | thoracic | 0 | CHAR MODIF |
| SBE | lumbar | 0 | CHAR MODIF |
| SBF | lumbosacral | 0 | CHAR MODIF |
| SBG | pelvic | 0 | CHAR MODIF |
| SBH | sacral | 0 | CHAR MODIF |
| SBI | right rotation | 0 | CHAR MODIF |
| SBJ | head | 0 | CHAR MODIF |
| SBK | occipital | 0 | CHAR MODIF |
| SBL | parieto-temporal | 0 | CHAR MODIF |

TABLE 1-continued

BARCODES - KEYWORDS - DESCRIPTIVE TEXT

| BAR | FULL TEXT | PCT | STAT TYPE |
|---|---|---|---|
| SBM | frontal | 0 | CHAR MODIF |
| SBN | facial | 0 | CHAR MODIF |
| SBO | shoulder | 0 | CHAR MODIF |
| SBP | arm | 0 | CHAR MODIF |
| SBQ | wrist | 0 | CHAR MODIF |
| SBR | hand | 0 | CHAR MODIF |
| SBS | finger | 0 | CHAR MODIF |
| SBT | hip | 0 | CHAR MODIF |
| SBU | buttocks | 0 | CHAR MODIF |
| SBV | leg | 0 | CHAR MODIF |
| SBW | knee | 0 | CHAR MODIF |
| SBX | ankle | 0 | CHAR MODIF |
| SBY | foot | 0 | CHAR MODIF |
| SBZ | toe | 0 | CHAR MODIF |
| SCA | breast | 0 | CHAR MODIF |
| SCB | abdominal | 0 | CHAR MODIF |
| SCC | genital | 0 | CHAR MODIF |
| SCD | groin | 0 | CHAR MODIF |
| SCE | positive or abnormal | 0 | CHAR MODIF |
| SCF | negative or normal | 0 | CHAR MODIF |
| SCG | increased | 0 | CHAR MODIF |
| SCH | decreased | 0 | CHAR MODIF |
| SCI | absent | 0 | CHAR MODIF |
| SCJ | start | 0 | CHAR MODIF |
| SCK | continue | 0 | CHAR MODIF |
| SCL | increase | 0 | CHAR MODIF |
| SCM | decrease | 0 | CHAR MODIF |
| SCN | discontinue | 0 | CHAR MODIF |
| SCO | Patient's progress is affected by | 9 | CHAR MODIF |
| SCP | left rotation | 0 | CHAR MODIF |
| SCQ | right lateral flexion | 0 | CHAR MODIF |
| SCR | left lateral flexion | 0 | CHAR MODIF |
| SCS | and | 0 | CHAR MODIF |
| SCT | | 0 | CUST MODIF |
| SCU | | 0 | CUST MODIF |
| SCV | | 0 | CUST MODIF |
| SCW | | 0 | CUST MODIF |
| SCX | | 0 | CUST MODIF |
| SCY | | 0 | CUST MODIF |
| SCZ | | 0 | CUST MODIF |
| SDA | | 0 | CUST MODIF |
| SDB | | 0 | CUST MODIF |
| SDC | | 0 | CUST MODIF |
| SEA | Patient entered the office complaining of | 9 | CHAR S-INIT |
| SEB | Patient also complained of | 9 | CHAR S-INIT |
| SEC | Patient reported | 9 | CHAR S-INIT |
| SED | During today's visit, the patient discussed having | 9 | CHAR S-INIT |
| SEE | [*SEE.DOCTOR*] | 0 | CHAR S-INIT |
| SEF | | 9 | CUST S-INIT |
| SFF | stabbing pain | 1 | CHAR SUBJ |
| SFG | sharp pain | 1 | CHAR SUBJ |
| SFH | pain | 1 | CHAR SUBJ |
| SFI | aching | 1 | CHAR SUBJ |
| SFJ | headache | 1 | CHAR SUBJ |
| SFK | tenderness | 1 | CHAR SUBJ |
| SFL | soreness | 1 | CHAR SUBJ |
| SFM | weakness | 1 | CHAR SUBJ |
| SFN | hyperesthesia | 1 | CHAR SUBJ |
| SFO | paresthesia | 1 | CHAR SUBJ |
| SFP | hypesthesia | 1 | CHAR SUBJ |
| SFQ | sensations of heat | 1 | CHAR SUBJ |
| SFR | sensations of cold | 1 | CHAR SUBJ |
| SFS | sciatica | 1 | CHAR SUBJ |
| SFT | | 1 | CUST SUBJ |
| SFU | | 1 | CUST SUBJ |
| SFV | splinting | 1 | CHAR SUBJ |
| SFW | range of motion decreased | 1 | CHAR SUBJ |
| SFX | stiffness | 1 | CHAR SUBJ |
| SFY | aberrant motion | 1 | CHAR SUBJ |
| SFZ | antalgia | 1 | CHAR SUBJ |
| SGA | | 1 | CUST SUBJ |
| SGB | | 1 | CUST SUBJ |
| SGC | | 1 | CUST SUBJ |
| SGD | swelling | 1 | CHAR SUBJ |
| SGE | redness or flushing | 1 | CHAR SUBJ |
| SGF | blanching | 1 | CHAR SUBJ |
| SGG | discoloration | 1 | CHAR SUBJ |
| SGH | bruising | 1 | CHAR SUBJ |
| SGI | inflammation | 1 | CHAR SUBJ |
| SGJ | infection | 1 | CHAR SUBJ |
| SGK | open sores | 1 | CHAR SUBJ |
| SGL | vertigo | 1 | CHAR SUBJ |
| SGM | nervousness | 1 | CHAR SUBJ |
| SGN | tension | 1 | CHAR SUBJ |
| SGO | tinnitus | 1 | CHAR SUBJ |
| SGP | vision irregularities | 1 | CHAR SUBJ |
| SGQ | fatigue | 1 | CHAR SUBJ |
| SGR | depression | 1 | CHAR SUBJ |
| SGS | loss of sleep | 1 | CHAR SUBJ |
| SGT | breathing irregularities | 1 | CHAR SUBJ |
| SGU | digestive problems | 1 | CHAR SUBJ |
| SGV | diarrhea | 1 | CHAR SUBJ |
| SGW | constipation | 1 | CHAR SUBJ |
| SGX | defecation irregularities | 1 | CHAR SUBJ |
| SGY | urination problems | 1 | CHAR SUBJ |
| SGZ | fever | 1 | CHAR SUBJ |
| SHA | chills | 1 | CHAR SUBJ |
| SHB | during and/or after running | 2 | CHAR SUBJ |
| SHC | during and/or after walking | 2 | CHAR SUBJ |
| SHD | while standing | 2 | CHAR SUBJ |
| SHE | during lifting | 2 | CHAR SUBJ |
| SHF | upon bending | 2 | CHAR SUBJ |
| SHG | while sitting | 2 | CHAR SUBJ |
| SHH | while lying down | 2 | CHAR SUBJ |
| SHI | while sleeping | 2 | CHAR SUBJ |
| SHJ | upon rising | 2 | CHAR SUBJ |
| SHK | following a cough or sneezing | 2 | CHAR SUBJ |
| SHL | after meals | 2 | CHAR SUBJ |
| SHM | | 2 | CUST SUBJ |
| SHN | | 2 | CUST SUBJ |
| SHO | | 2 | CUST SUBJ |
| SHP | | 2 | CUST SUBJ |
| SHQ | | 2 | CUST SUBJ |
| SHR | | 7 | CUST SUBJ |
| SHS | | 7 | CUST SUBJ |
| SHT | | 7 | CUST SUBJ |
| SHU | | 7 | CUST SUBJ |
| SHV | | 7 | CUST SUBJ |
| SHW | | 7 | CUST SUBJ |
| SHX | | 7 | CUST SUBJ |
| SHY | | 7 | CUST SUBJ |
| SHZ | | 7 | CUST SUBJ |
| SIA | | 7 | CUST SUBJ |
| SIB | | 7 | CUST SUBJ |
| SIC | | 7 | CUST SUBJ |
| SID | | 7 | CUST SUBJ |
| SIE | | 7 | CUST SUBJ |
| SIF | | 7 | CUST SUBJ |
| SIG | | 7 | CUST SUBJ |
| SIH | | 7 | CUST SUBJ |
| SII | | 7 | CUST SUBJ |
| SIJ | | 7 | CUST SUBJ |
| SIK | | 7 | CUST SUBJ |
| SIL | | 7 | CUST SUBJ |
| SIM | | 7 | CUST SUBJ |
| SIN | | 7 | CUST SUBJ |
| SIO | | 7 | CUST SUBJ |
| SIP | | 7 | CUST SUBJ |
| SIQ | | 7 | CUST SUBJ |
| SIR | | 7 | CUST SUBJ |
| SIS | | 7 | CUST SUBJ |
| SIT | | 7 | CUST SUBJ |
| SIU | | 7 | CUST SUBJ |
| SIV | | 7 | CUST SUBJ |
| SIW | | 7 | CUST SUBJ |
| SJF | Examination of the patient revealed | 9 | CHAR O-INIT |
| SJG | Today the patient exhibited | 9 | CHAR O-INIT |
| SJH | Patient also exhibited | 9 | CHAR O-INIT |
| SJI | [*SEE.DOCTOR*] | 0 | CHAR O-INIT |
| SJJ | | 9 | CUST O-INIT |
| SJK | | 9 | CUST O-INIT |
| SKF | head tilt | 3 | CHAR OBJ |
| SKG | high shoulder | 3 | CHAR OBJ |
| SKH | low shoulder | 3 | CHAR OBJ |
| SKI | scoliosis | 3 | CHAR OBJ |

TABLE 1-continued
BARCODES - KEYWORDS - DESCRIPTIVE TEXT

| BAR | FULL TEXT | PCT | STAT TYPE |
|---|---|---|---|
| SKJ | kyphosis | 3 | CHAR OBJ |
| SKK | lordosis | 3 | CHAR OBJ |
| SKL | hip higher than the other hip | 3 | CHAR OBJ |
| SKM | hip lower than the other hip | 3 | CHAR OBJ |
| SKN | a short right leg | 3 | CHAR OBJ |
| SKO | a long right leg | 3 | CHAR OBJ |
| SKP | a short left leg | 3 | CHAR OBJ |
| SKQ | a long left leg | 3 | CHAR OBJ |
| SKR | a balanced leg length | 3 | CHAR OBJ |
| SKS | a normal gait | 3 | CHAR OBJ |
| SKT | an abnormal gait | 3 | CHAR OBJ |
| SKU |  | 3 | CUST OBJ |
| SKV | increased heat reading by instrument | 3 | CHAR OBJ |
| SKW | heat instrument readings similar to prior readings | 3 | CHAR OBJ |
| SKX | decreased heat reading by instrument | 3 | CHAR OBJ |
| SKY | heat instrument readings which are normal | 3 | CHAR OBJ |
| SKZ |  | 3 | CUST OBJ |
| SLA |  | 3 | CUST OBJ |
| SLB |  | 3 | CUST OBJ |
| SLC |  | 3 | CUST OBJ |
| SLD | swelling | 3 | CHAR OBJ |
| SLE | redness or flushing | 3 | CHAR OBJ |
| SLF | blanching | 3 | CHAR OBJ |
| SLG | discoloration | 3 | CHAR OBJ |
| SLH | bruising | 3 | CHAR OBJ |
| SLI | inflammation | 3 | CHAR OBJ |
| SLJ | infection | 3 | CHAR OBJ |
| SLK | open sore | 3 | CHAR OBJ |
| SLL | muscle spasm | 3 | CHAR OBJ |
| SLM | a taut muscle bundle | 3 | CHAR OBJ |
| SLN | muscle flaccidity | 3 | CHAR OBJ |
| SLO | muscle weakness | 3 | CHAR OBJ |
| SLP | tenderness | 3 | CHAR OBJ |
| SLQ | strain | 3 | CHAR OBJ |
| SLR | sprain | 3 | CHAR OBJ |
| SLS | subluxation complex | 3 | CHAR OBJ |
| SLT | splinting | 3 | CHAR OBJ |
| SLU | rigidity | 3 | CHAR OBJ |
| SLV | range of motion limitation | 3 | CHAR OBJ |
| SLW | range of motion decreased | 3 | CHAR OBJ |
| SLX | range of motion within normal limits | 3 | CHAR OBJ |
| SLY | range of motion increased | 3 | CHAR OBJ |
| SLZ | range of motion to be aberrant | 3 | CHAR OBJ |
| SMA | antalgia | 3 | CHAR OBJ |
| SMB | foramina compression | 4 | CHAR OBJ |
| SMC | shoulder depression | 4 | CHAR OBJ |
| SMD | Adson's | 4 | CHAR OBJ |
| SME | biceps reflex | 4 | CHAR OBJ |
| SMF | triceps reflex | 4 | CHAR OBJ |
| SMG | brachioradialis reflex | 4 | CHAR OBJ |
| SMH | patellar reflex | 4 | CHAR OBJ |
| SMI | achilles reflex | 4 | CHAR OBJ |
| SMJ | Rhombergs | 4 | CHAR OBJ |
| SMK | Adam's | 4 | CHAR OBJ |
| SML | Ely's | 4 | CHAR OBJ |
| SMM | Goldthwaite | 4 | CHAR OBJ |
| SMN | Laseque's | 4 | CHAR OBJ |
| SMO | Braggard's | 4 | CHAR OBJ |
| SMP | Leg raiser | 4 | CHAR OBJ |
| SMQ | Leg lower | 4 | CHAR OBJ |
| SMR | Fabere Patrick's | 4 | CHAR OBJ |
| SMS | Soto Hall | 4 | CHAR OBJ |
| SMT | Trendelenburg's | 4 | CHAR OBJ |
| SMU |  | 7 | CUST OBJ |
| SMV |  | 7 | CUST OBJ |
| SMW |  | 7 | CUST OBJ |
| SMX |  | 7 | CUST OBJ |
| SMY |  | 7 | CUST OBJ |
| SMZ |  | 7 | CUST OBJ |
| SNA |  | 7 | CUST OBJ |
| SNB |  | 7 | CUST OBJ |
| SNC |  | 7 | CUST OBJ |
| SND |  | 7 | CUST OBJ |
| SNE |  | 7 | CUST OBJ |
| SNF |  | 7 | CUST OBJ |
| SNG |  | 7 | CUST OBJ |
| SNH |  | 7 | CUST OBJ |
| SNI |  | 7 | CUST OBJ |
| SNJ |  | 7 | CUST OBJ |
| SNK |  | 7 | CUST OBJ |
| SNL |  | 7 | CUST OBJ |
| SNM |  | 7 | CUST OBJ |
| SNN |  | 7 | CUST OBJ |
| SNO |  | 7 | CUST OBJ |
| SNP |  | 7 | CUST OBJ |
| SNQ |  | 7 | CUST OBJ |
| SNR |  | 7 | CUST OBJ |
| SOA | The patient is | 9 | CHAR A-INIT |
| SOB | The patient appears to be | 9 | CHAR A-INIT |
| SOC | [*SEE.DOCTOR*] | 0 | CHAR A-INIT |
| SOD |  | 9 | CUST A-INIT |
| SPD | progressing as anticipated | 5 | CHAR ASSESS |
| SPE | progressing slowly but steadily | 5 | CHAR ASSESS |
| SPF | progressing slower than anticipated | 5 | CHAR ASSESS |
| SPG | making no measurable progress | 5 | CHAR ASSESS |
| SPH | exhibiting symptoms consistent with the inital diagnosis | 5 | CHAR ASSESS |
| SPI | exhibiting symptoms consistent with the updated diagnosis | 5 | CHAR ASSESS |
| SPJ |  | 5 | CUST ASSESS |
| SPK |  | 5 | CUST ASSESS |
| SPL | not stationary | 5 | CHAR ASSESS |
| SPM | stationary | 5 | CHAR ASSESS |
| SPN | at a stage of maximum medical improvement | 5 | CHAR ASSESS |
| SPO | 5%-10% improved | 5 | CHAR ASSESS |
| SPP | 10%-20% improved | 5 | CHAR ASSESS |
| SPQ | 20%-30% improved | 5 | CHAR ASSESS |
| SPR | 30%-40% improved | 5 | CHAR ASSESS |
| SPS | 40%-50% improved | 5 | CHAR ASSESS |
| SPT | 50%-60% improved | 5 | CHAR ASSESS |
| SPU | 60%-70% improved | 5 | CHAR ASSESS |
| SPV | 70%-80% improved | 5 | CHAR ASSESS |
| SPW | 80%-90% improved | 5 | CHAR ASSESS |
| SPX | 90+% improved | 5 | CHAR ASSESS |
| SPY | 100% improved | 5 | CHAR ASSESS |
| SPZ | progressing rapidly | 5 | CHAR ASSESS |
| SQA | discharged as cured | 5 | CHAR ASSESS |
| SQB | age | 6 | CHAR ASSESS |
| SQC | weight | 6 | CHAR ASSESS |
| SQD | work | 6 | CHAR ASSESS |
| SQE | physical activity | 6 | CHAR ASSEss |
| SQF | minor reinjury | 6 | CHAR ASSESS |
| SQG | reinjury | 6 | CHAR ASSESS |
| SQH | structural degeneration | 6 | CHAR ASSESS |
| SQI | stress | 6 | CHAR ASSESS |
| SQJ | chronicity | 6 | CHAR ASSESS |
| SQK |  | 6 | CUST ASSESS |
| SQL |  | 6 | CUST ASSESS |
| SQM |  | 7 | CUST ASSESS |
| SQN |  | 7 | CUST ASSESS |
| SQO |  | 7 | CUST ASSESS |
| SQP |  | 7 | CUST ASSESS |
| SQQ |  | 7 | CUST ASSESS |
| SQR |  | 7 | CUST ASSESS |
| SQS |  | 7 | CUST ASSESS |
| SQT |  | 7 | CUST ASSESS |
| SQU |  | 7 | CUST ASSESS |
| SQV |  | 7 | CUST ASSESS |
| SQW |  | 7 | CUST ASSESS |
| SQX |  | 7 | CUST ASSESS |
| STD | Patient should | 9 | CHAR P-INIT |
| STE | [*SEE.DOCTOR*] | 0 | CHAR P-INIT |
| STF |  | 9 | CUST P-INIT |
| STG |  | 9 | CUST P-INIT |
| SUC | be seen twice daily | 8 | CHAR PLAN |
| SUD | return in one day | 8 | CHAR PLAN |
| SUE | return in two days | 8 | CHAR PLAN |
| SUF | return in three days | 8 | CHAR PLAN |
| SUG | return in four days | 8 | CHAR PLAN |
| SUH | return in five days | 8 | CHAR PLAN |
| SUI | return in six days | 8 | CHAR PLAN |

TABLE 1-continued
BARCODES - KEYWORDS - DESCRIPTIVE TEXT

| BAR | FULL TEXT | PCT | STAT | TYPE |
|---|---|---|---|---|
| SUJ | return in one week | 8 | | CHAR PLAN |
| SUK | return in 10 days | 8 | | CHAR PLAN |
| SUL | return in two weeks | 8 | | CHAR PLAN |
| SUM | return in three weeks | 8 | | CHAR PLAN |
| SUN | return in four weeks | 8 | | CHAR PLAN |
| SUO | return in one month | 8 | | CHAR PLAN |
| SUP | return in two months | 8 | | CHAR PLAN |
| SUQ | return in three months | 8 | | CHAR PLAN |
| SUR | return in four months | 8 | | CHAR PLAN |
| SUS | return in six months | 8 | | CHAR PLAN |
| SUT | return in nine months | 8 | | CHAR PLAN |
| SUU | return in one year | 8 | | CHAR PLAN |
| SUV | return in two years | 8 | | CHAR PLAN |
| SUW | return as needed | 8 | | CHAR PLAN |
| SUX | maintain the same schedule | 8 | | CHAR PLAN |
| SUY | stay with the schedule as planned | 8 | | CHAR PLAN |
| SUZ | therapy | 8 | | CHAR PLAN |
| SVA | rehabilitation | 8 | | CHAR PLAN |
| SVB | exercise | 8 | | CHAR PLAN |
| SVC | nutrition | 8 | | CHAR PLAN |
| SVD | the use of orthotics | 8 | | CHAR PLAN |
| SVE | lab tests | 8 | | CHAR PLAN |
| SVF | work release | 8 | | CHAR PLAN |
| SVG | work restrictions | 8 | | CHAR PLAN |
| SVH | be referred to another D.C. | 8 | | CHAR PLAN |
| SVI | be referred to a M.D. | 8 | | CHAR PLAN |
| SVJ | be referred to the hospital | 8 | | CHAR PLAN |
| SVK | be referred to a physical therapist | 8 | | CHAR PLAN |
| SVL | | 7 | | CUST PLAN |
| SVM | | 7 | | CUST PLAN |
| SVN | | 7 | | CUST PLAN |
| SVO | | 7 | | CUST PLAN |
| | ... blank line ... leave blank or enter a code | 0 | | CHAR |

APPENDIX A

```c
#include <stdio.h>
#include <stdlib.h>
#include <memory.h>
#include <string.h>
#include <graph.h>
#include <malloc.h>
#include <pi.h>

/* c version of c_soap and associated subroutines
    using the R-base programmable interface
    written by Craig Gissler
    loosely based on version written in R-Base (r) Microrim Inc.
    by Dave Hamilton and Phil Harris
    Copyright (c) S.O.A.P NOTES, INC. 1989
*/ typedef struct
{       /* scodes row storage */
        char    scode[4];       /* code on chart that is scanned */
        char    type[12];       /* modifier, adjective, noun, phrase, etc.*/
        char    sdesc[70];      /* actual phrase used in combining w/ others */
        char    keyword[30];    /* chart word */
        long    pct;            /* numeric type of phrase indicator */
        char    status[4];      /* i.e. cust, futu */
} SCODES_ROW;
SCODES_ROW   scodes_b, *scodes_rp;

typedef struct
{       /* scodary element */
        char    scode[6];       /**/
        char    sdesc[72];      /* extra length for string handling */
        long    pct;            /**/
} SCOD;

typedef struct
{    /* processing element */
  char  scode[4];
  long  pct;
  char  sdesc[72];
} PROCESS_EL;

typedef struct
{ /* dictate row storage, note is ultimately stored here when processed */
        long    visit;
        char    comment[800];
} DICTATE_ROW;
DICTATE_ROW   dictate_b, *dictate_rp;

typedef struct
{       /* dictate row text buffers for non text fields */
        char    visit[8];
} DICTATEBUFF;
DICTATEBUFF   dictate_e;

typedef struct
{       /* dictate row storage */
        long    visit;
        char    comment[1500];
```

```c
} LONG_ROW;
LONG_ROW    long_b, *long_rp;

typedef struct
(       /* visit row storage */
        char    pcode[8];       /* patient bar code */
        DATE    pdate;          /* date note scanned */
        TIME    ptime;          /* time note scanned */
        long    visit;          /* number of visit for indexing */
        char    doctor[12];     /* doctor who examinned patient */
        long    pct;            /* numeric type of phrase indicator */
) VISIT_ROW;
VISIT_ROW   visit_b, *visit_rp;

typedef struct
(       /* visit edit buffer, text fields for non-text elements */
        char    pdate[30];
        char    ptime[20];
        char    visit[8];
        char    pct[8];
) VISITBUFF;
VISITBUFF   visit_e;

typedef struct
(       /* vdata row storage, general purchaser info */
        long    vline;          /* index */
        long    visit;          /* number of visits stored */
        char    l1[60];         /* name of user */
        char    l2[60];         /* address and */
        char    l3[60];         /* other user */
        char    l4[60];         /* info */
        DATE    pdate;          /* purchase date */
        char    snumber[8];     /* serial number */
        char    status[4];      /* indicates path or starting point for jumping
                                   in and out of different exe parts of program */
        char    prtr[4];        /* which printer to use lpt1, etc */
        long    bvisit;         /* last visit processed time before processing
                                   begins each download (to determine which range
                                   of visits processed in most recent download */
) VDATA_ROW;
VDATA_ROW   vdata_b, *vdata_rp;

typedef struct
(       /* vdata text buffers for non-numeric items */
        char    vline[8];
        char    visit[8];
        char    pdate[30];
        char    bvisit[8];
) VDATABUFF;
VDATABUFF   vdata_e;

typedef struct
(       /* pat row storage */
        char    patcode[8];     /* patient bar code */
        char    patacct[12];    /* patient account number */
        char    lnme[30];       /* last name */
        char    fnme[30];       /* first name */
        char    fullnme[60];    /* full name */
        char    addr[40];       /* address */
        char    city[16];
        char    state[4];       /* 2 char in rb form */
        char    zipcode[12];
        char    group[4];       /* 1 char in rb form -- insurance type indicator */
) PAT_ROW;
PAT_ROW     pat_b, *pat_rb;

typedef struct
(       /* doctor row storage */
        char    wandid[10];     /* wand identification index, to match */
        char    doctor[12];     /* doctor doing examination */
) DOCTOR_ROW;
DOCTOR_ROW  doctor_b, *doctor_rb;
#define ESC        27   /* ESCape key */
#define R_ARROW    77   /* cursor control */
#define L_ARROW    75
#define U_ARROW    72
#define D_ARROW    80
#define ENTER      13

SCODES_ROW      scode_buff;
#define NUMSCODES  776  /* maximum number of scode that memory can hold */
```

```
SCOD    scodary[NUMSCODES];   /* for in memory match of wand visit info
                                 with phrases for processing of visit notes */
int scode_limit = NUMSCODES - 1; /* last scodary index */

/* VVV pointers to r-base tables in spnotes database */
RELATION *relp, *phist_p, *repdata_p, *vdata_p, *groups_p, *scodes_p,
         *doctor_p, *visit_p, *dictate_p, *long_p, *pat_p;
char *locklst[15]; /* list of pointers to tables locked form multi users */

DATABASE *dbp;         /* pointer to r-base database "SPNOTES" */
RELINFO  *dictate_r, *visit_r, *long_r;  /* internal r-base table info */
ATTINFO  *dictate_a, *visit_a, *long_a;  /* internal r_base attribute in
                                            a specific table info */ int     stat = 0;       /*      error status   */
char    blank=' ';      /*      blank constant */
int     fldno,retkey,x,y;
float   cresult;
int     i,notelen,newnlen,recno,exitflg;
char    ch;
int      select=0;
int     choice, choice2, form_opt, sort_opt;
char    datestr[32],    /* computer's date, date of download/processing */
        timestr[22],    /* computer's time, time of '' */
        blankstr[80],
        str[40],        /* general text buffer */
        wandid_old[12],/* current wand being processed */
        wand_scode[4]; /* scode taken from one line of download of wand */

FILE *wstream;          /* download file */ void load_scodes(void);
void process_notes(void);
int find_scode(char *,int,int);
void pcode_or_scode(void);

main()
{
/* VVVV general house keeping -- preparing r-base data base facilities for
        processing of notes. R-BASE facilites are not essential to processing
        of notes.  It just happens to be the data base used.

end of house keeping indicated by ^^^^ */

_clearscreen(_GCLEARSCREEN);
  printf("(c) Copyright 1988, 1989, S. O. A. P. Notes, Inc., Lincoln, NE.\n");
  printf("All rights reserved.\n");
  _strdate(datestr);
  _strtime(timestr);
  rbstart();

dbp = NULL;
  rbset(dbp,"set MULTI on");
  if (rberrmsg(&stat))
  {
    printf("ERROR on rb set MULTI - %d\n",stat);
    ch = getch();
    exit(stat);
  } /* end if (rberrmsg */ dbp = rbopen("SPNOTES");
  if (rberrmsg(&stat))
  {
    printf("error on rbopen - %d\n",stat);
    ch = getch();
    exit(stat);
  } /* end if (rberrmsg */
printf(" memavail - %u ",_memavl());

/* rbset(dbp,"set autoskip on");
*/
  rbset(dbp,"set bell on");
  if (rberrmsg(&stat))
  {
    printf("error on set - %d\n",stat);
    ch = getch();
    exit(stat);
  } /* end if (rberrmsg */ printf("Processing Notes, Interrupting WILL Corrupt Your Data!! Please Wait.
/*^^^^*/
  process_notes();
```

```
/*VVVVVV closing and exitting data base (to end of main procedure)*/ rbclsrel(dictate_p);
  if (rberrmsg(&stat))
  {
    printf("ERROR on rb clsrel - DICTATE, %d\n",stat);
  } /* end if (rberrmsg */
  rbclsrel(visit_p);
  if (rberrmsg(&stat))
  {
    printf("ERROR on rb clsrel - VISIT, %d\n",stat);
  } /* end if (rberrmsg */
  rbclose(dbp);
  if (rberrmsg(&stat))
  {
    printf("ERROR on rb close - SPNOTES, %d\n",stat);
  } /* end if (rberrmsg */
  exit(0);
} /* end main */ void load_scodes(void)
/* The purpose of this procedure is to place all of the essential infomation,
   phrases, matching scode indecies, and phrase type in memory for fast
   access.  This information will ultimatelly be matched with information
   from the 'wand.txt' download.
*/
{
  scodes_p = rbopnrel(dbp,"SCODES");
  if (rberrmsg(&stat))
  {
    printf("error on rb openrel - %d\n",stat);
    exit(stat);
  } /* end if (rberrmsg */ exitflg = 0;
  recno = 0;
  for(rbgetrow(scodes_p,(char *)&scodes_b); !rberrm_(&stat) && !exitflg;
     rbgetrow(scodes_p,(char *)&scodes_b))
  {
    for(i = 0; i < sizeof(scodes_b.scode); i++)
    {
      scodary[recno].scode[i] = scodes_b.scode[i];
    } /* end for(i */
    scodary[recno].scode[4] = '\0';
    for(i = 0; i < sizeof(scodes_b.sdesc); i++)
    {
      scodary[recno].sdesc[i] = scodes_b.sdesc[i];
    } /* end for (i */
    for(i = (sizeof(scodary[recno].sdesc) -3);
        (scodary[recno].sdesc[i] == ' ') && (i>-1); i--);
      scodary[recno].sdesc[i+1] = '\0';

scodary[recno].pct = scodes_b.pct;
    recno++;
  } /* end for */
  scode_limit = recno - 1; /* !!! candidate for pass back - last scode read*/
} /* end load_scodes */ void process_notes(void)
/* The purpose of this procedure is to match info in the 'wand.txt' download
   file with the scode information loaded in memory, construct the phrases
   and sentences by adding puctuation, and store them in a "note" */
{
  char visitstr[10], vstr[1500];
  static char wherestr[80];
  int endlist = 0;
  int exitct = 4;
  int recno = -1;
  int cnt, nc;
  int invalid_seedoc_flag;
  PROCESS_EL process[4];

/* the VDATA information will likely be loaded already as part of startup
   tasks of the program as a whole. As long as we break out to down load,
   steps will have to be taken to ensure info is not lost.
*/
  memset(visit_e.pdate,' ',sizeof(visit_e.pdate));  /* clear buffers */
  memset(visit_e.ptime,' ',sizeof(visit_e.ptime));

strcpy(wherestr, "where VLINE eq 1");          /* get user/system info */
  vdata_p = rbopnrel(dbp,"VDATA");
  if (rberrmsg(&stat))
```

```
{
  printf("ERROR on rb openrel VDATA - %d\n",stat);
  ch = getch();
  exit(stat);
} /* end if (rberrmsg */ rbwhere(vdata_p, wherestr);
if (rberrmsg(&stat))
{
  printf("ERROR on rb where VDATA - %d \n",stat);
  ch = getch();
  exit(stat);
} /* end if (rberrmsg */ rbgetrow(vdata_p, (char *)&vdata_b);
if (rberrmsg(&stat))
{
  printf("ERROR on rb getrow VDATA = %d \n",stat);
  ch = getch();
  exit(stat);
} /* end if (rberrmsg */
/*printf("vdata.visit at open - %d \n",vdata_b.visit);
*/
  vdata_b.bvisit = vdata_b.visit;
/*  the needed system info needed is the last visit stored, 'vdata_b.visit',
    which will be saved as the beginning of the process visit range,
    'vdata_b.bvisit'. Vdata_b.visit will be incremented and indicate the
    end of the range after processing.
*/ load_scodes();

/* r-base open storage tables for notes --
   Notes are stored in a VISIT DICTATE pair, for short notes, and VISIT LONG
   pair for longer notes. This storage routine is not essential to the
   processing. Other more unified/uniform methods are being developed.
*/ dictate_p = rbopnrel(dbp,"DICTATE");
  if (rberrmsg(&stat))
  {
    printf("ERROR on rb openrel DICTATE - %d \n",stat);
    ch = getch();
    exit(stat);
  } /* end if (rberrmsg */
  strcpy(wherestr,"where VISIT eq ");
  itoa((vdata_b.visit - 1),visitstr,10);
  strcat(wherestr,visitstr);
  rbwhere(dictate_p,wherestr);  /*"where COUNT eq LAST");*/
  if (rberrmsg(&stat))
  {
    printf("ERROR on rb where DICTATE - %d\n",stat);
    ch = getch();
    exit(stat);
  } /* end if (rberrmsg */

/*  HOW TO TEST FOR INFORMATION ON RELATION PARAMS  (debug info)
dictate_r = rbrelinf(dbp,"DICTATE");
printf("%s wid %d natt %d nrow %d \n",
    dictate_r->name, dictate_r->rowwid, dictate_r->natt, dictate_r->nrow);
free(dictate_r);
dictate_a = rbattinf(dbp,"DICTATE","VISIT");
printf("name %s loc %d typ %d len %d key %d\n",
 dictate_a->name,dictate_a->loc,dictate_a->typ,dictate_a->len,dictate_a->key);
free(dictate_a);
dictate_a = rbattinf(dbp,"DICTATE","COMMENT");
printf("name %s loc %d typ %d len %d key %d\n",
 dictate_a->name,dictate_a->loc,dictate_a->typ,dictate_a->len,dictate_a->key);
free(dictate_a);
ch = getch();
*/ long_p = rbopnrel(dbp,"LONG");
  if (rberrmsg(&stat))
  {
    printf("ERROR on rb openrel LONG - %d \n",stat);
    ch = getch();
    exit(stat);
  } /* end if (rberrmsg */
  rbwhere(long_p,wherestr); /*"where COUNT eq LAST");*/
  if (rberrmsg(&stat))
```

```c
{
  printf("ERROR on rb where LONG - %d\n",stat);
  ch = getch();
  exit(stat);
  } /* end if (rberrmsg */ visit_p = rbopnrel(dbp,"VISIT");
  if (rberrmsg(&stat))
  {
    printf("error on rb openrel VISIT - %d\n",stat);
    ch = getch();
    exit(stat);
  } /* end if (rberrmsg */
  rbwhere(visit_p,wherestr); /*"where COUNT eq LAST");*/
  if (rberrmsg(&stat))
  {
    printf("ERROR on rb where VISIT - %d\n",stat);
    ch = getch();
    exit(stat);
  } /* end if (rberrmsg */
  visit_r = rbrelinf(dbp,"VISIT");
  printf("%10d Visits Currently Stored\n",visit_r->nrow);
  printf("%10ld = Last Visit #\n",vdata_b.visit-1);
  free(visit_r);

/* ^^^^end of r_base opening note tables */

/* vvvv info matching wand id from download in wand.txt to the examining
           doctor
*/ doctor_p = rbopnrel(dbp,"DOCTOR");
  if (rberrmsg(&stat))
  {
    printf("error on rb openrel DOCTOR - %d\n",stat);
    exit(stat);
  } /* end if (rberrmsg */

/* vvvv locking of r-base tables for multi-user use */
  ch = 'Y';
  while ((ch == 'Y') || (ch == 'y'))
  {
    ch = 'N';
    locklst[0] = vdata_p;
    locklst[1] = visit_p;
    locklst[2] = dictate_p;
    locklst[3] = long_p;
    locklst[4] = (char *) 0;
    rblock(locklst);
    if (rberrmsg(&stat))
      if (stat = 500)
      {
        printf("DB in use.  Try again?  Y/N\n");
        ch = getch();
        if ((ch != 'y') || (ch != 'Y'))
          exit(stat);
      }
      else
      {
        printf("ERROR on rb lock - %d\n",stat);
        ch = getch();
        exit(stat);
      } /* end if (rberrmsg */
  } /* end while (ch */

/*printf(" memavail - %u ",_memavl());  debug info */ if ((wstream = fopen("wand.txt","r")) == NULL)
  {
    printf("ERROR opening wand.txt: ");
  } /* end if (rberrmsg */
  else
  {
    do
    { /* find first pcode record */
      fgets(str,sizeof(str),wstream);
    } /* end do while ferror/feof/'P' */
    while (!ferror(wstream) && !feof(wstream) && (str[26] != 'P'));

cnt = 0;
    while (!ferror(wstream) && !feof(wstream))
```

```c
      (/* enter with first pcode, set up visit, pass to bottom for 1st scode */
      pcode_or_scode();
/* init process */
      memset(process[0].scode,' ',sizeof(process[0].scode));
      memset(process[0].sdesc,' ',sizeof(process[0].sdesc));
      process[0].pct = -2;  /* pct = -2 means do nothing with this record */
      for (i=1; i<4; i++)
      {
        process[i] = process[(i-1)];
      } /* end for */
      memset(vstr,' ',sizeof(vstr));
      vstr[0] = '\0';
      exitct = 4;
      invalid_seedoc_flag = 0;

/* ready to process current note */ while (exitct)
      {
/**/    if ((process[0].pct != 11) &&
          !((process[3].pct == 99) || (process[2].pct == 99)))
        {
          switch((short)process[3].pct)
          {
            case -2: break;
            case -1: if ((strlen(vstr)+26) < 1500) /* scode was not found */
                     {                             /*print error */
                       strcat(vstr," [Invalid Scan Code -    ] ");
                       memcpy(&vstr[(strlen(vstr)-5)],process[3].scode,3);
                     } /* end if */               /*wand_scode^^^ not found */
                     else
                     {                             /* note to long, print error */
                       if (strlen(vstr) > (1500-16))
                       {
                         vstr[(1500-16)] = '\0';
                       } /* end if */
                       strcat(vstr,"NOTE TRUNCATED");
                     } /* end else */
                     if (!invalid_seedoc_flag)    /* error condition set */
                       invalid_seedoc_flag = 1;
                     /* set flag */
                     break;
            case 7:                               /* cases for full sentences, no puntuation needed */
            case 9: if ((strlen(vstr) != 0) && (strlen(vstr) < (1500 - 2)))
                      if (vstr[(strlen(vstr)-1)] != '.')
                        strcat(vstr, ".");
            default:
/*                case 0,1,2,3,4,5,6,8,10:
*/              if (process[3].pct == 10)  /* set see doc flag index */
                {                         /* for quick review/attention after process */
                  if (!invalid_seedoc_flag)
                    invalid_seedoc_flag = 1;
                  /* set flag */
                }
                if (vstr[0] != '\0')
                  strcat(vstr, " ");
                if ((strlen(vstr) + strlen(process[3].sdesc) + 10) < 1500)
                {         /* with in not length limits */
                  strcat(vstr, process[3].sdesc);

if ((process[3].pct == 0) || (process[3].pct == 7) ||
                      (process[3].pct == 9))
                    break;      /* these pcts need no puntuation ^^^*/
                  /* otherwise check to see if multiple of same pct
                     in buffer and puctuate accordingly,
                     more than 2 same requires commma,
                     2 only requires 'and'
                  */
                  if (process[2].pct == process[3].pct)
                    if (process[1].pct == process[3].pct)
                    {
                      strcat(vstr, ",");
                    } /* end if process[1] == process[3] */
                    else
                    {
                      strcat(vstr, " and");
                      if (process[2].pct == 5)
                        strcat(vstr, " is");
                    } /* end else process[1] != process[3] */
                } /* end if (strlen... */
                else
                {         /* error - note too long */
                  if (strlen(vstr) > (1500-16))
```

```c
            {
                vstr[(1500-16)] = '\0';
            } /* end if */
            strcat(vstr,"NOTE TRUNCATED");
            if (!invalid_seedoc_flag)
                invalid_seedoc_flag = 1;
          } /* end else */
          break;
      } /* end switch process[3].pct */
    } /* end if (process[0].pct */ if (exitct == 4)           /* ensure last 3 scodes processed */
    {                          /* without flowing into next visit */
/*if pcode get scod prepare to fall out
if eof prepare to fall out (count down one)
*/
        fgets(str,sizeof(str),wstream);
        if (feof(wstream))
        {
          exitct--;
          for (i=3; i>0; i--)
            process[i] = process[(i-1)];
          process[0].pct = -2;
        /* dont want to exit, may just be end of table */
        } /* end if (feof */
        else if (ferror(wstream))
        {
          perror("ERROR on wand.txt gets: ");
          exit(0);
        } /* end if (ferror */
        else if (str[26] == 'P')
        {
          exitct--;     /*  end of visit note, fill buff w/ dummy no-oop */
          for (i=3; i>0; i--)
            process[i] = process[(i-1)];
          process[0].pct = -2;
        } /* end else if (str */
        else
        {           /* load next scode */
          memcpy(wand_scode,&str[31],3);
          recno = find_scode(wand_scode, 0,scode_limit);
          if (recno != -1)   /* -1 indicates error -- not found */
          {
/**/        if ((process[0].pct == 11) && (scodary[recno].pct == 11))
            {    /* undo last scan processing, program will just
                    loop and slide pct == 11 out without processing */
              strcat(process[0].sdesc,scodary[recno].sdesc);
            } /* end if ((process */
            else /* slide scodes in buff, lose last [3] < just processed */
            {
              for (i=3; i>0; i--)
                process[i] = process[(i-1)];
              process[0].pct = scodary[recno].pct;
              memcpy(process[0].scode,scodary[recno].scode,
                     sizeof(process[0].scode));
              memcpy(process[0].sdesc,scodary[recno].sdesc,
                     sizeof(process[0].sdesc));
              for (i=(sizeof(process[0].sdesc)-1);
                     process[0].sdesc[i] == ' '; i--);
              process[0].sdesc[i+1] = '\0';
            } /* end else ...((process[0].pct */
          } /* end if (recno */
          else
          {
            for (i=3; i>0; i--)
              process[i] = process[(i-1)];
            process[0].pct = -1;       /* will be flagged and printed as
                                          and error when reaches position 3 */
            memcpy(process[0].scode,wand_scode,3);
            process[0].scode[4] = '\0';
            process[0].sdesc[0] = '\0';
          } /* end else recno == 1 */
        } /* end else */
    } /* end if exitct ==4 */
    else
    {
        exitct--;                       /* end of note fill with no-op */
        for (i=3; i>0; i--)
          process[i] = process[(i-1)];
        process[0].pct = -2;
    } /* end else exitct < 4 */
  } /* end while */
```

```
/* processing of current note done exept for final punctuation and storage*/
/* check last char for '.' */
       if (!ferror(wstream) || (ferror(wstream) && feof(wstream)))
       {
          if (strlen(vstr) > 0)
          {
             if (vstr[(strlen(vstr)-1)] != '.')
                strcat(vstr, ".");
          } /* end if */
/*                            store note in VISIT and (DICTATE or LONG)*/
          if (strlen(vstr) <= 800)
          {
             memset(&vstr[strlen(vstr)],' ',1);
             dictate_b.visit = visit_b.visit;
             memcpy(dictate_b.comment,vstr,sizeof(dictate_b.comment));
             rbaddrow(dictate_p,(char *)&dictate_b);
             if (rberrmsg(&stat))
             {
                printf("ERROR on rb addrow DICTATE- %d visit %d \n",stat, dictate_b
                ch = getch();
                exit(stat);
             } /* end if (rberrmsg */ visit_b.pct = 99 - (invalid_seedoc_flag*2);
          } /* end if (str */
          else
          {
             memset(&vstr[strlen(vstr)],' ',1);
             long_b.visit = visit_b.visit;
             memcpy(long_b.comment,vstr,sizeof(long_b.comment));

rbaddrow(long_p,(char *)&long_b);
             if (rberrmsg(&stat))
             {
                printf("ERROR on rb addrow LONG- %d visit %d \n",stat,long_b.visit)
                ch = getch();
                exit(stat);
             } /* end if (rberrmsg */ visit_b.pct = 98 - (invalid_seedoc_flag*2);
          } /* end else if (strlen */ rbaddrow(visit_p,(char *)&visit_b);
          if (rberrmsg(&stat))
          {
             printf("ERROR on rb addrow VISIT- %d visit - %d \n", stat,visit_b.vis
             ch = getch();
             exit(stat);
          } /* end if (rberrmsg */
/*                          store current visit count */
          rbputrow(vdata_p, (char *)&vdata_b);
          if (rberrmsg(&stat))
          {
             printf("ERROR on rb putrow VDATA = %d \n",stat);
             ch = getch();
             exit(stat);
          } /* end if */
          else
          {
             rbdatflush(dbp,vdata_p);
             if (rberrmsg(&stat))
             {
                printf("ERROR on rb datflush VISIT- %d\n",stat);
                exit(stat);
             } /* end if (rberrmsg */
          } /* end else rberr putrow */

/*                              display count info */
          if (++cnt%10 == 0)
          {
             _settextposition(6,1);
             printf("%10d Notes Processed\n",cnt);
          } /* end if cnt */
       } /* end if (!ferror */
    } /* end while outter */
/*                             end of processing store last visit count */
    rbputrow(vdata_p, (char *)&vdata_b);
    if (rberrmsg(&stat))
```

```c
    {
      printf("ERROR on rb putrow VDATA = %d \n",stat);
      ch = getch();
      exit(stat);
    } /* end if (rberrmsg */
                    /* close download file and display processing numbers */
    fclose(wstream);

visit_r = rbrelinf(dbp,"VISIT");
    _settextposition(6,1);
    printf("%10d Notes Processed\n",cnt);
    printf("Done Processing!!!\n");
    printf("%10d Visits Currently Stored\n",visit_r->nrow);
    printf("%10ld = Last Visit #\n",vdata_b.visit-1);
    free(visit_r);
  } /* end else wand.txt opened */
  rbunlock(locklst);

} /* end process_notes */ void pcode_or_scode(void)
/*   The purpose of this procedure is to test a line from the download
     file 'wand.txt' to see whether it contains a P or S code. (pcode-
     indicates a new patient or note to be processed, scode- indicates
     continuation of same note).  If it is a pcode, a check of the wandid
     is also made to see if processing of a new wand has begun.  If it has
     the new doctor is matched and loaded into a buffer for storing with
     the  VISIT information.
*/

{
  char *wandid_new = NULL;
  char *token = NULL;
  char wherestr[40];
  if (str[26] == 'P')   /* is it a pcode? */
  {
    strcpy(visit_e.pdate,strtok(str," "));       /* date of visit retrieved */
    str[strlen(visit_e.pdate)] = ' ';
    a_att(visit_e.pdate,(char *)&visit_b.pdate,4,30);

strcpy(visit_e.ptime,strtok(NULL," "));      /* time of visit retrieved */
    str[strlen(visit_e.ptime)] = ' ';
    a_att(visit_e.ptime,(char *)&visit_b.ptime,5,20);
    wandid_new = strtok(NULL," ");               /* wandid retrieved */
    if (strcmp(wandid_new,wandid_old) != 0)      /* comparison of current
                                                    and new id */
    {
      strcpy(wherestr, "where WANDID eq ");      /* if different retrieve */
      strcat(wherestr,wandid_new);               /* new doctor name */
      rbwhere(doctor_p,wherestr);
      if (rberrmsg(&stat))
      {
        printf("ERROR on rb where '%s' = %d \n", wherestr, stat);
        ch = getch();
        exit(stat);
      } /* end if (rberrmsg */ rbgetrow(doctor_p,(char *)&doctor_b);
      if (rberrmsg(&stat))
      {
        memcpy(visit_b.doctor," unknown     ",12);
      } /* end if (rberrmsg */
      else
      {
        memcpy(visit_b.doctor,doctor_b.doctor,12);
      } /* end else not err */
      strcpy(wandid_old,wandid_new);
    } /* end if wand new != old */ memcpy(visit_b.pcode,strtok(NULL," "),8);  /* patient barcode retrieved */
        visit_b.visit = vdata_b.visit++;           /* incr visit counter */
    } /* end if (str[26] = 'P') */

} /* end pcode_or_scode */ int find_scode(char *target,int left, int right)
{ /* binary search to find scode information in memory*/
    int midpt,rel;
```

```
midpt = (left + right) / 2;
rel = memcmpi(target,scodary[midpt].scode,3);
if (left > right)
   return (-1);
else if (rel == 0)
   return (midpt);
else if (rel < 0)
   return (find_scode(target,left,midpt-1));
else if (rel > 0)
   return (find_scode(target,midpt+1,right));
} /* find_scode */
```

We claim:

1. An apparatus for recording progress notes, comprising a bar code input data source including a plurality of bar codes indicative of preassigned input information, at least some of said bar codes being indicative of information in a form selected from the group consisting of words and phrases, a computer having memory means and programmable data processing means, input means operative to scan selected bar codes of said data source and to input the scanned codes into said computer memory means, said programmable data processing means being operative to compile and edit said scanned codes, including the scanned codes of the aforementioned some of said bar codes so as to generate full text progress notes, in complete sentences, of the preassigned input information indicated by said scanned codes, said programmable data processing means being operative to assign a respective numeric value to each scanned code and to then edit each scanned codes as a function of the numeric value thereof.

2. The apparatus of claim 1 wherein said input means comprises a portable wand operative to scan, store and download into said computer memory, a plurality of bar codes from said bar code input data source.

3. The apparatus of claim 2 wherein said bar code input data source comprises a wall chart.

4. The apparatus of claim 2 wherein said input means further comprises a combination recharger/downloader electrically connectable to said computer and a source of electric power and operative to removably receive said wand for recharging it and downloading scanned bar codes therefrom.

5. The apparatus of claim 1 wherein the bar codes of said bar code input data source are arranged in subsets according to subject matter classifications.

6. The apparatus of claim 5 wherein a substantial portion of said bar codes are indicative of input information relating to a field of use selected from the group consisting of a medical practice, a law practice, building construction and catering service.

7. The apparatus of claim 1 wherein said numeric values are operative to cause editing of the type selected from the group consisting of the injection of punctuation, the addition of conjectives or conjective phrases and phrase rearrangement.

8. The apparatus of claim 7 wherein said programmable data processing means is operative to translate the scanned and edited codes to the respective preassigned input information indicated by them.

9. A method for recording progress notes, comprising providing a bar code input data source including a plurality of bar codes indicative of respective preassigned input information relating to a progressing factual situation, at least some of said bar codes being indicative of information in a form selected from the group consisting of words and phrases, providing a computer having a memory means and a programmable data processing means, providing a bar code reader, examining said progressing factual situation, proposing a treatment for said progressing factual situation, scanning, with said bar code scanner, selected bar codes of said bar code input data source which are descriptive of the examined condition of said progressing factual situation and the proposed treatment thereof, downloading said bar code reader, thereby imputting said scanned codes into said computer memory means, causing said programmable data processing means to compile and edit said scanned codes, including the scanned codes of the aforementioned some of said bar codes, so as to generate full text progress notes, in complete sentences, of the preassigned input information indicated by said scanned codes, and said causing step comprising assigning a respective numeric value to each scanned code and then editing said scanned codes as a function of the numeric value thereof.

10. The method of claim 9 wherein scanning selected bar codes comprises storing the scanned codes in said bar code reader.

11. The method of claim 9 further comprising arranging said bar code input data source at the site of said examining step and said scanning step is performed during said examining and proposing steps.

12. The method of claim 9 further comprising arranging the bar codes on said bar code input data source in subsets according to subject matter classifications.

13. The method of claim 9 wherein said editing step comprises editing of the type selected from the group consisting of injecting punctuation, adding conjectives or conjective phrases and rearranging phrases.

14. The method of claim 13 wherein said causing step includes translating the scanned and edited codes into the respective preassigned input information indicated by them.

15. The method of claim 9 wherein said step of providing a bar code reader comprises providing a rechargeable bar code reader and further comprising recharging said bar code reader after said downloading step.

16. An apparatus for recording progress notes, comprising a bar code input data source including a plurality of bar codes indicative of preassigned input information, at least some of said bar codes being indicative of information in a form selected from the group consisting of words and phrases, a computer having memory means and programmable data processing means, input means operative to scan selected bar codes of said data source and to input the scanned codes into said computer memory means, said programmable data processing means being operative to compile and edit said scanned codes, including the scanned codes of the aforementioned some of said bar codes so as to generate full text progress notes, in complete sentences, of the preassigned input information indicated by said scanned codes, said programmable data processing means being operative to assign a respective numeric value to each scanned code and to then edit each of the scanned codes as a function of the numeric value thereof, and said numeric values being operative to cause editing of the type selected from the group consisting of the injection of punctuation the addition of conjectives or conjective phrases or phrase rearrangement.

17. An apparatus for recording progress notes, comprising a bar code input data source including a plurality of bar codes indicative of preassigned input information, at least some of said bar codes being indicative of information in a form selected from the group consisting of words and phrases, a computer having memory means and programmable data processing means, input means operative to scan selected bar codes of said data source and to input the scanned codes into said computer memory means, said programmable data processing means being operative to compile and edit said scanned codes, including the scanned codes of the aforementioned some of said bar codes so as to generate full text progress notes, in complete sentences, of the preassigned input information indicated by said scanned codes, said programmable data processing means being operative to assign a respective numeric value to each scanned code and to the edit each of the scanned codes as a function of the numeric value thereof, said numeric values being operative to cause editing of the type selected from the group consisting of the injection of punctuation, the addition of conjectives or conjective phrases or phrase rearrangement, and said programmable data processing means being operative to output the preassigned input information corresponding to said scanned codes in complete sentence form.

* * * * *